United States Patent [19]

Kuhnt et al.

[11] Patent Number: 5,273,958
[45] Date of Patent: Dec. 28, 1993

[54] SUBSTITUTED TRIAZOLINONES

[75] Inventors: Dietmar Kuhnt, Leverkusen;
Klaus-Helmut Müller, Duesseldorf;
Kurt Findeisen, Leverkusen; Klaus
König, Odenthal; Klaus Lürssen,
Bergisch Gladbach; Hans-Joachim
Santel, Leverkusen; Robert R.
Schmidt, Bergisch Gladbach, all of
Fed. Rep. of Germany

[73] Assignee: Bayer Aktiengesellschaft,
Leverkusen, Fed. Rep. of Germany

[21] Appl. No.: 871,788

[22] Filed: Apr. 20, 1992

[30] Foreign Application Priority Data

Apr. 30, 1991 [DE] Fed. Rep. of Germany ....... 4114074

[51] Int. Cl.$^5$ ................. A01N 43/653; C07D 249/12
[52] U.S. Cl. .................................... 504/139; 548/263.8
[58] Field of Search ................... 548/263.8; 71/92

[56] References Cited

U.S. PATENT DOCUMENTS 4,076,938 2/1978 Böhner et al. ............... 548/263.8
4,931,084 6/1990 Findeisen et al. ........... 548/263.8

FOREIGN PATENT DOCUMENTS 0294666 5/1988 European Pat. Off. .
0370293 11/1989 European Pat. Off. .
399294 11/1990 European Pat. Off. .

OTHER PUBLICATIONS

Chemical Abstracts Service CA 114:143425a, 1990.

*Primary Examiner*—Marianne M. Cintins
*Assistant Examiner*—Catherine S. Kilby Scalzo
*Attorney, Agent, or Firm*—Sprung Horn Kramer & Woods

[57] ABSTRACT

The invention relates to novel substituted triazolinones of the general formula (I)

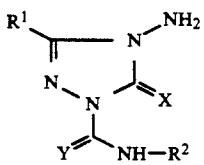

in which $R^1$ represents alkyl or cycloalkyl, $R^2$ represents cycloalkyl which is optionally substituted by aryl, arylalkyl, arylalkenyl or arylalkinyl, or represents a radical of the formula

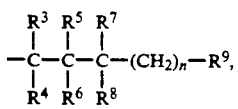

X represents oxygen or sulphur and
Y represents oxygen or sulphur, where
$R^3$, $R^4$, $R^5$, $R^6$, $R^7$ and $R^8$ represent hydrogen or alkyl,
$R^9$ represents in each case optionally substituted cycloalkyl, aryl or heteroaryl and
n represents a number 0, 1, 2 or 3, but with the exception of those compounds in which, simultaneously, $R^1$ represents a methyl radical, X represents oxygen, Y represents oxygen and $R^2$ represents a radical of the formula

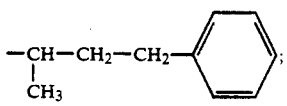

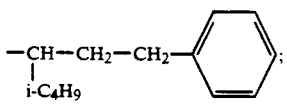

(Abstract continued on next page.)

-continued
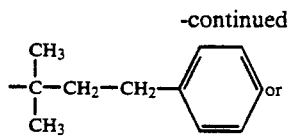 or
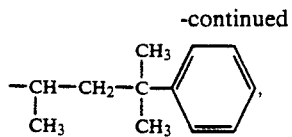,
a plurality of processes and novel intermediates for their preparation, and their use as herbicides.
13 Claims, No Drawings

SUBSTITUTED TRIAZOLINONES

The invention relates to new substituted triazolinones, to a plurality of processes and novel intermediates for their preparation, and to their use as herbicides.

It has been disclosed that certain substituted triazolinones, such as, for example, the compound 1-(4-phenyl-2-butylaminocarbonyl)-3-methyl-4-amino-1,2,4-triazolin-5-one, have herbicidal properties (compare, for example, DE-OS (German Published Specification) 3,719,575).

However, the herbicidal activity of these previously known compounds against problem weeds and their compatibility with important crop plants are not entirely satisfactory in all fields of application.

There have now been found new substituted triazolinones of the general formula (I)

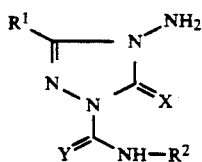

in which
$R^1$ represents alkyl or cycloalkyl,
$R^2$ represents cycloalkyl which is optionally substituted by aryl, arylalkyl, arylalkenyl or arylalkinyl, or represents a radical of the formula

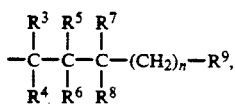

X represents oxygen or sulphur and
Y represents oxygen or sulphur, where
$R^3$, $R^4$, $R^5$, $R^6$, $R^7$ and $R^8$ represent hydrogen or alkyl,
$R^9$ represents in each case optionally substituted cycloalkyl, aryl or heteroaryl and
n represents a number 0, 1, 2 or 3,
but with the exception of those compounds in which, simultaneously, $R^1$ represents a methyl radical, X represents oxygen, Y represents oxygen and $R^2$ represents a radical of the formula

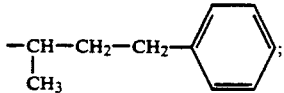

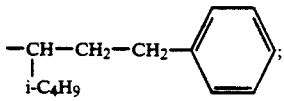

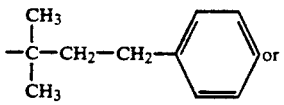

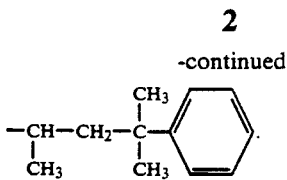

The compounds of the formula (I) can optionally be present as geometric and/or optical isomers or isomer mixtures of different composition depending on the nature of the substituents $R^1$ and $R^2$. Both the pure isomers and the isomer mixtures are claimed according to the invention.

Furthermore, it has been found that the new substituted triazolinones of the general formula (I)

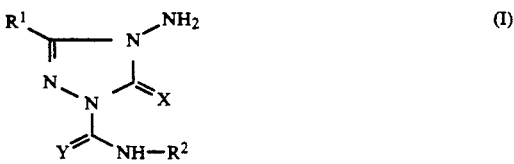

in which
$R^1$ represents alkyl or cycloalkyl,
$R^2$ represents cycloalkyl which is optionally substituted by aryl, arylalkyl, arylalkenyl or arylalkinyl, or represents a radical of the formula

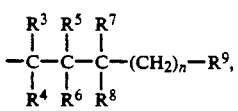

X represents oxygen or sulphur and
Y represents oxygen or sulphur,
where
$R^3$, $R^4$, $R^5$, $R^6$, $R^7$ and $R^8$ represent hydrogen or alkyl,
$R^9$ represents in each case optionally substituted cycloalkyl, aryl or heteroaryl and
n represents a number 0, 1, 2 or 3,
but with the exception of those compounds in which, simultaneously, $R^1$ represents a methyl radical, X represents oxygen, Y represents oxygen and $R^2$ represents a radical of the formula

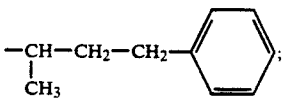

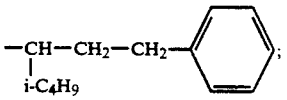

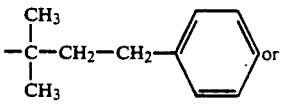

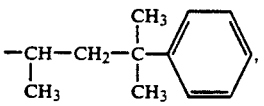

are obtained when
a) hydrazones of the formula (II)

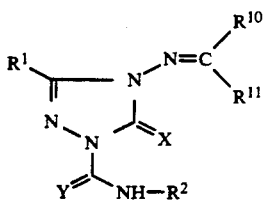

in which
R¹, R², X and Y have the abovementioned meaning and
R¹⁰ and R¹¹ independently of one another in each case represent hydrogen, alkyl, aralkyl or aryl,
are reacted with an acid, if appropriate in the presence of a diluent,
or when
b) 1H-triazolinones of the formula (III),

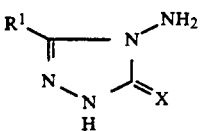

in which
R¹ and X have the abovementioned meaning,
are reacted with iso(thio)cyanates of the formula (IV),

in which
R² and Y have the abovementioned meaning,
if appropriate in the presence of a diluent and if appropriate in the presence of a reaction auxiliary,
or when
c) triazolinones of the formula (V),

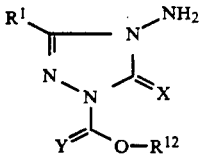

in which
R¹, X and Y have the abovementioned meaning and
R¹² represents alkyl, aralkyl or aryl,
are reacted with amines of the formula (VI),

in which
R² has the abovementioned meaning,
if appropriate in the presence of a diluent and if appropriate in the presence of a reaction auxiliary.

Finally, it has been found that the new substituted triazolinones of the general formula (I) have herbicidal properties.

Surprisingly, the substituted triazolinones of the general formula (I) according to the invention show a considerably more powerful herbicidal activity against problem weeds while simultaneously having an equally good compatibility with important crop plants when compared with the substituted triazolinones which are known from the prior art, such as, for example, the compound 1-(4-phenyl-2-butylaminocarbonyl)-3-methyl-4-amino-1,2,4-triazolin-5-one, which are similar compounds chemically and from the point of view of their actions.

Formula (I) provides a general definition of the substituted triazolinones according to the invention. Preferred compounds of the formula (I) are those in which
R¹ represents a straight-chain or branched alkyl having 1 to 6 carbon atoms or cycloalkyl having 3 to 7 carbon atoms,
R² represents cycloalkyl which has 3 to 7 carbon atoms and which is optionally monosubstituted or polysubstituted by identical or different substituents, suitable substituents being:
aryl, arylalkyl, arylalkenyl or arylalkinyl, each of which has 6 or 10 carbon atoms in the aryl moiety and, if appropriate, up to 6 carbon atoms in the respective straight-chain or branched alkyl or alkenyl or alkinyl moieties and each of which is optionally monosubstituted or polysubstituted by identical or different substituents, suitable aryl substituents in each case being:
halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted or polysubstituted by identical or different substituents from the series comprising halogen and/or straight-chain or branched alkyl having 1 to 4 carbon atoms,
R² furthermore represents a radical of the formula

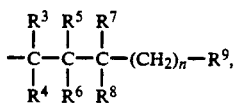

X represents oxygen or sulphur and
Y represents oxygen or sulphur, where
R³ represents straight-chain or branched alkyl having 1 to 8 carbon atoms,
R⁴, R⁵, R⁶, R⁷ and R⁸ independently of each other in each case represent hydrogen or straight-chain or branched alkyl having 1 to 4 carbon atoms,
R⁹ represents cycloalkyl which has 3 to 7 carbon atoms and which is optionally monosubstituted or poly-substituted by identical or different substituents, suitable substituents being:
halogen, cyano, in each case straight-chain or branched alkyl having 1 to 4 carbon atoms and in each case straight-chain or branched halogenoalkyl having in each case 1 to 4 carbon atoms and 1 to 9 identical or different halogen atoms;
R⁹ furthermore represents aryl which has 6 to 10 carbon atoms or heteroaryl which has 2 to 9 carbon atoms and 1 to 4 identical or different hetero atoms, in particular nitrogen, oxygen and/or sulphur, each of these aryl or heteroaryl radicals being optionally monosubstituted or polysubstituted by identical or different substituents, suitable substituents in each case being:

halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms; divalent, straight-chain or branched dioxyalkylene which has 1 to 3 carbon atoms and which is optionally monosubstituted to tetrasubstituted by identical or different halogen substituents; dialkylamino, N-alkanoylamino, alkoxycarbonyl or alkoximinoalkyl, each of which has 1 to 4 carbon atoms in individual straight-chain or branched alkyl moieties, and aryl or aryloxy which has 6 or 10 carbon atoms and which is in each case optional)y monosubstituted or polysubstituted by identical or different substituents from the series comprising halogen and/or straight-chain or branched alkyl having 1 to 4 carbon atoms, and n represents a number 0, 1, 2 or 3;

but with the exception of those compounds in which, simultaneously, $R^1$ represents a methyl radical, X represents oxygen, Y represents oxygen and $R^2$ represents a radical of the formula

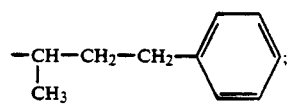

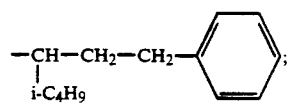

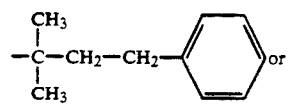

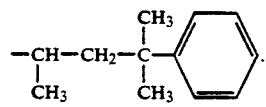

Particularly preferred compounds of the formula (I) are those in which $R^1$ represents methyl, ethyl, n- or i-propyl, n-, i-, s-or t-butyl, cyclopropyl, cyclobutyl, cyclopentyl or cyclohexyl, $R^2$ represents cyclopropyl, cyclobutyl, cyclopentyl or cyclohexyl, each of which is optionally monosubstituted to disubstituted by identical or different substituents, suitable substituents in each case being:

phenyl, benzyl, phenylethyl, phenylpropyl, phenylethenyl, phenylpropenyl, phenylethinyl, phenylpropinyl, α-naphthyl or β-naphthyl, each of which is optionally monosubstituted to trisubstituted in the aryl moiety by identical or different substituents, suitable aryl substituents in each case being: fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl, or phenyl which is optionally monosubstituted to trisubstituted by identical or different substituents from the series comprising fluorine, chlorine, bromine, methyl and/or ethyl, $R^2$ furthermore represents a radical of the formula

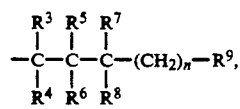

X represents oxygen or sulphur and

Y represents oxygen or sulphur, where $R^3$ represents straight-chain or branched alkyl having 1 to 6 carbon atoms, $R^4$, $R^5$, $R^6$, $R^7$ and $R^8$ represent hydrogen or straight-chain or branched alkyl having 1 to 3 carbon atoms, $R^9$ represents cyclopropyl, cyclobutyl, cyclopentyl or cyclohexyl, each of which is optionally monosubstituted to pentasubstituted by identical or different substituents, suitable substituents in each case being: fluorine, chlorine, bromine, cyano, methyl, ethyl, n- or i-propyl, chloromethyl, dichloromethyl, trichloromethyl, difluoromethyl or trifluoromethyl; $R^9$ furthermore represents phenyl, α-naphthyl, β-naphthyl, pyridyl, pyrimidyl, triazinyl, pyridazinyl, pyrazolyl, imidazolyl, triazolyl, thiazolyl, isothiazolyl, benzthiazolyl, oxazolyl, isoxazolyl, benzoxazolyl, benzopyrazolyl, pyrrolyl, furanyl, thienyl, indoyl, benzopyranyl or quinolyl, each of which is optionally monosubstituted to trisubstituted by identical or different substituents, suitable substituents in each case being:

fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, difluoromethyl, trifluoromethyl, difluoromethoxy, trifluoromethoxy, difluoromethylthio, trifluoromethylthio, dimethylamino, diethylamino, N-acetamido, dioxymethylene, difluorodioxymethylene, dioxyethylene, trifluorodioxyethylene, tetrafluorodioxyethylene, methoxycarbonyl, ethoxycarbonyl, propoxycarbonyl, methoximinomethyl, methoximinoethyl, ethoximinomethyl, ethoximinoethvl, or phenyl, phenoxy, α-naphthyl or β-naphthyl each of which is optionally monosubstituted to trisubstituted by identical or different substituents from the series comprising fluorine, chlorine, bromine, methyl, ethyl, methoxy and/or ethoxy, and n represents a number 0, 1 or 2, but with the exception of those compounds in which, simultaneously, $R^1$ represents a methyl radical, X represents oxygen, Y represents oxygen and $R^2$ represents a radical of the formula

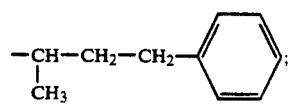

-continued $$-\underset{\underset{i-C_4H_9}{|}}{CH}-CH_2-CH_2-\text{Ph};$$

$$-\underset{\underset{CH_3}{|}}{\overset{\overset{CH_3}{|}}{C}}-CH_2-CH_2-\text{Ph} \text{ or}$$

$$-\underset{\underset{CH_3}{|}}{CH}-CH_2-\underset{\underset{CH_3}{|}}{\overset{\overset{CH_3}{|}}{C}}-\text{Ph}.$$

Very particularly preferred compounds of the formula (I) are those in which $R^1$ represents methyl, ethyl, n- or i-propyl or cyclopropyl, $R^2$ represents a radical of the formula $$-\underset{\underset{R^4}{|}}{\overset{\overset{R^3}{|}}{C}}-\underset{\underset{R^6}{|}}{\overset{\overset{R^5}{|}}{C}}-\underset{\underset{R^8}{|}}{\overset{\overset{R^7}{|}}{C}}-(CH_2)_n-R^9,$$

X represents oxygen,
Y represents oxygen,
$R^3$ represents methyl, ethyl, n- or i-propyl, n-, i-, s-or t-butyl,
$R^4$, $R^5$, $R^6$, $R^7$ and $R^8$ independently of each other in each case represent hydrogen, methyl or ethyl,
$R^9$ represents phenyl which is optionally monosubstituted to trisubstituted by identical or different substituents, suitable substituents in each case being:
fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, difluoromethyl, trifluoromethyl, difluoromethoxy, trifluoromethoxy, difluoromethylthio, trifluoromethylthio, dimethylamino, diethylamino, N-acetamido, dioxymethylene, difluorodioxymethylene, dioxyethylene, trifluorodioxyethylene, tetrafluorodioxyethylene, methoxycarbonyl, ethoxycarbonyl, propoxycarbonyl, methoximinomethyl, methoximinoethyl, ethoximinomethyl, ethoximinoethyl, or phenyl, phenoxy, α-naphthyl or β-naphthyl, each of which is optionally monosubstituted to trisubstituted by identical or different substituents from the series comprising fluorine, chlorine, bromine, methyl, ethyl, methoxy and/or ethoxy, and
n represents a number 0 or 1,
but with the exception of those compounds in which, simultaneously, $R^1$ represents a methyl radical, X represents oxygen, Y represents oxygen and $R^2$ represents a radical of the formula $$-\underset{\underset{CH_3}{|}}{CH}-CH_2-CH_2-\text{Ph};$$

$$-\underset{\underset{i-C_4H_9}{|}}{CH}-CH_2-CH_2-\text{Ph};$$

$$-\underset{\underset{CH_3}{|}}{\overset{\overset{CH_3}{|}}{C}}-CH_2-CH_2-\text{Ph} \text{ or}$$

$$-\underset{\underset{CH_3}{|}}{CH}-CH_2-\underset{\underset{CH_3}{|}}{\overset{\overset{CH_3}{|}}{C}}-\text{Ph}.$$

Compounds which may be mentioned individually are those which are listed in the Preparation Examples.

If, for example, 1-{N-[4-(4-chlorophenyl)-2-methyl-but-2-yl]-carbamoyl}-4-isopropylideneimino-3-methyl-1,2,4-triazolin-5-one is used as starting compound, the course of the reaction of process (a) according to the invention can be outlined by the following equation:

[Structure of starting triazolinone with isopropylideneimino group and N-[4-(4-chlorophenyl)-2-methyl-but-2-yl]-carbamoyl substituent]

$$\xrightarrow[-(CH_3)_2CO]{+ H_2O/H^+}$$

[Structure of product: 4-amino-triazolinone with carbamoyl substituent]

If, for example, 4-amino-3-methyl-1,2,4-(1H)-triazolin-5-one and 3-methyl-4-phenyl-but-2-yl isocyanate are used as starting substances, the course of the reaction of process (b) according to the invention can be outlined by the following equation:

[Structure of 4-amino-3-methyl-triazolinone] +

$$O=C=N-\underset{\underset{CH_3}{|}}{CH}-\underset{\underset{CH_3}{|}}{CH}-CH_2-\text{Ph} \longrightarrow$$

-continued

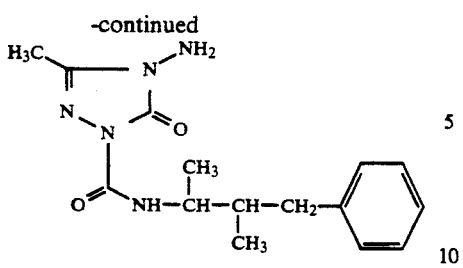

If, for example, 1-ethoxycarbonyl-4-amino-3-methyl-1,2,4-triazolin-5-ore and 4-phenyl-2-ethyl-but-2-ylamine are used as starting substances, the course of the reaction of process (c) according to the invention can be outlined by the following equation:

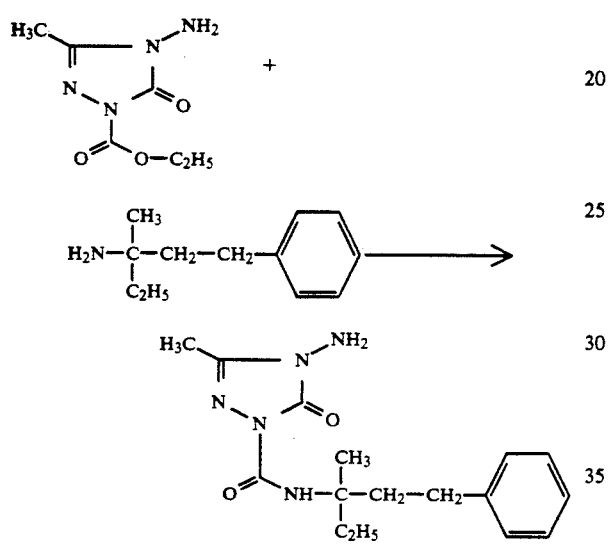

Formula (II) provides a general definition of the hydrazones required as starting substances for carrying out process (a) according to the invention. In this formula (II), $R^1$, $R^2$, X and Y preferably represent those radicals which have already been mentioned in connection with the description of the compounds of the formula (I) according to the invention as being preferred for these substituents. $R^{10}$ and $R^{11}$ preferably represent, in each case independently of one another, hydrogen, straight-chain or branched alkyl having 1 to 4 carbon atoms, phenyl or benzyl.

The hydrazones of the formula (II) were hitherto unknown. They are also a subject of the present invention. They are obtained in analogy to known processes (compare, for example, DE-OS (German Published Specification) 3,803,523 or Acta. Pol. Pharm. 38, 153–162 [1981] or CA 95: 203841), for example when 1H-triazolinones of the formula (III)

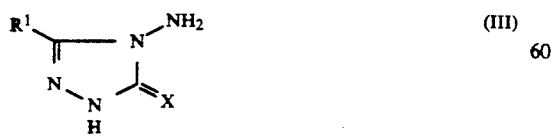

in which
$R^1$ and X have the abovementioned meaning
are reacted with aldehydes or ketones of the formula (VII)

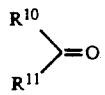 (VII)

in which
$R^{10}$ and $R^{11}$ have the abovementioned meaning,
if appropriate in the presence of a diluent such as, for example, dichloromethane or toluene and, if appropriate, in the presence of a reaction auxiliary such as, for example, p-toluenesulphonic acid, at temperatures between 40° C. and 120° C., and the resulting 1-unsubstituted triazolinone-hydrazones of the formula (VIII)

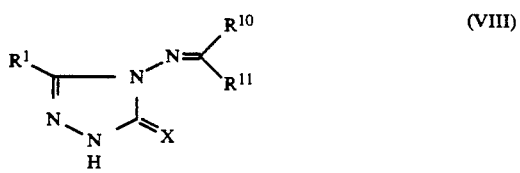

in which
$R^1$, $R^{10}$, $R^{11}$ and X have the abovementioned meaning,
are reacted either, in a subsequent 2nd step, with iso(thio)cyanates of the formula (IV),

in which
$R^2$ and Y have the abovementioned meaning,
if appropriate in the presence of a diluent such as, for example, dichloromethane or dioxane and, if appropriate, in the presence of a reaction auxiliary such as, for example, triethylamine, at temperatures between 0° C. and 150° C., or, alternatively, in a subsequent 2nd step, with (thio)chloroformic esters of the formula (IX)

in which
$R^{12}$ represents alkyl, aralkyl or aryl and
Y has the abovementioned meaning,
or with (thio)phosgene, if appropriate in the presence of a diluent such as, for example, chloroform, dichloromethane or tetrahydrofuran, and, if appropriate, in the presence of a reaction auxiliary such as, for example, triethylamine, sodium hydride or potassium tert-butylate, at temperatures between −20° C. and +100° C., and the resulting triazolinone derivatives of the formula (X),

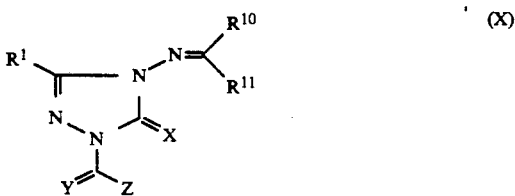

in which

Z represents a radical —O—$R^{12}$ or chlorine and
$R^1$, $R^{10}$, $R^{11}$, X and Y have the abovementioned meaning, are reacted, in a subsequent 3rd step, with amines of the formula (VI)

$$R^2-NH_2 \quad\quad (VI)$$

in which
$R^2$ has the abovementioned meaning,
if appropriate in the presence of a diluent such as, for example, tetrahydrofuran and, if appropriate, in the presence of a reaction auxiliary such as, for example, sodium hydroxide or potassium hydroxide, at temperatures between 20° C. and 50° C..

Alternatively, triazolinone derivatives of the formula (X) are also obtained when triazolinones of the formula (V)

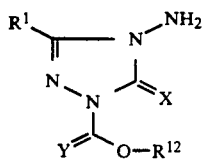

in which
$R^1$, X and Y have the abovementioned meaning and
$R^{12}$ represents alkyl, aralkyl or aryl,
are reacted with aldehydes or ketones of the formula (VII)

in which
$R^{10}$ and $R^{11}$ have the abovementioned meaning,
if appropriate in the presence of a diluent such as, for example, dichloromethane or toluene, and, if appropriate, in the presence of a reaction auxiliary such as, for example, p-toluenesulphonic acid, at temperatures between 40° C. and 120° C.

Formula (III) provides a general definition of the 1H-triazolinones required as starting materials for carrying out process (b) according to the invention and for the synthesis of the precursors of the formula (II). In this formula (III), $R^1$ and X preferably represent those radicals which have already been mentioned in connection with the description of the substances of the formula (I) according to the invention as being preferred for these substituents.

The 1H-triazolinones of the formula (III) are known or can be obtained in analogy to known processes (compare, for example, B.J. Heterocycl. Chem. 16, 403 [1979]; J. Heterocycl. Chem. 17, 1691 [1980]; Europ. J. Med. Chem. 18, 215 [1983]; Chem. Ber. 98, 3025 [1965]; Liebigs Ann. Chem. 637, 135 [1960]; DE-OS (German Published Specification) 3,719,575; DE-OS (German Published Specification) 3,803,523).

Formula (IV) provides a general definition of the iso(thio)cyanates furthermore required as starting materials for carrying out process (b) according to the invention and, if appropriate, for the synthesis of the precursors of the formula (II). In this formula (IV), $R^2$ and Y preferably represent those radicals which have already been mentioned in connection with the description of the substances of the formula (I) according to the invention as being preferred for these substituents.

Some of the iso(thio)cyanates of the formula (IV) are known (compare, for example, B. Nouv. J. Chim. 1,243-254 [1977] or CA 87: 151614a; U.S. Pat. No. 4,035,404) or can be obtained in analogy to known processes (compare, for example, Synthesis 1977, 756; Org. Syntheses Coll. Vol. IV, 521 [1963] or "Organikum" [Laboratory Practical Organic Chemistry] VEB Deutscher Verlag der Wissenschaften Berlin 1981, p. 703), for example when amines of the formula (VI)

$$R^2-NH_2 \quad\quad (VI)$$

in which
$R^2$ has the abovementioned meaning
are reacted with phosgene or thiophosgene, if appropriate in the presence of a diluent such as, for example, chloroform, toluene, chlorobenzene or tetrahydrofuran, and, if appropriate, in the presence of a reaction auxiliary such as, for example, triethylamine, sodium hydroxide or potassium hydroxide, at temperatures between −20° C. and +150° C.

Formula (V) provides a general definition of the triazolinones furthermore required as starting materials for carrying out process (c) according to the invention and, if appropriate, for the synthesis of the precursors of the formula (II). In this formula (V), $R^1$, X and Y preferably represent those radicals which have already been mentioned in connection with the description of the substances of the formula (I) according to the invention as being preferred for these substituents.

$R^{12}$ preferably represents straight-chain or branched alkyl having 1 to 4 carbon atoms, or represents phenyl or benzyl.

Triazolinones of the formula (V) are known or can be obtained in analogy to known processes (compare, for example, DE-OS (German Published Specification) 3,719,575; DE-OS (German Published Specification) 3,803,523).

Formula (VI) provides a general definition of the amines furthermore required as starting substances for carrying out process (c) according to the invention and, if appropriate, for the synthesis of the precursors of the formulae (II) and (IV). In this formula (VI), $R^2$ preferably represents those radicals which have already been mentioned in connection with the description of the compounds of the formula (I) according to the invention as being preferred for this substituent.

The amines of the formula (VI) are known or can be obtained in analogy to known processes (compare, for example, Coll. Czech. Chem. Commun. 35, 2810-2830 [1970]; Synth. Commun. 18, 29-35 [1988]; Angew. Chem. 96, 368-369 [1984]; DE-OS (German Published Specification) 2,825,961; DE-OS (German Published Specification) 3,222,152; U.S. Pat. No. 4,906,645; EP 320,898; U.S. Pat. No. 4,695,589; EP 237,305; U.S. Pat. No. 4,374,149; EP 28,105; EP 6,614; Nouv. J. Chim. 1, 243-254 [1977] or CA 87: 151614a).

Aldehydes and ketones of the formula (VII) are generally known compounds of organic chemistry.

(Thio-)chloroformic esters of the formula (IX) are also generally known compounds of organic chemistry.

Acids which are suitable for carrying out process (a) according to the invention are all inorganic or organic acids which can customarily be used for hydrazone cleavages. Inorganic mineral acids such as hydrochloric acid, sulphuric acid or phosphoric acid, are preferably used.

Diluents which are suitable for carrying out process (a) according to the invention are all customary organic or inorganic solvents. Solvents which are preferably used are polar organic solvents which are miscible with water, in particular alcohols such as methanol, ethanol, propanol or butanol, their mixtures with water, or pure water.

When carrying out process (a) according to the invention, the reaction temperatures can be varied within a substantial range. In general, the process is carried out at temperatures between +20° C. and +150° C., preferably at temperatures between +50° C. and +120° C.

Process (a) according to the invention is customarily carried out under atmospheric pressure or under reduced pressure. If it is carried out under reduced pressure, then suitable pressure ranges are those between 20 and 400 mbar, preferably between 100 and 200 mbar.

For carrying out process (a) according to the invention, 1.0 to 5.0 moles, preferably 1.0 to 2.5 moles, of acid are generally employed per mole of hydrazone of the formula (II). In this context, the hydrazone of the formula (II) is dissolved in a suitable amount of diluent, the required amount of acid is then added, and the mixture is slowly concentrated under reduced pressure over a period of several hours.

In a particular embodiment, it is also possible to carry out process (a) according to the invention and the preparation of the precursors of the formula (II) required for this process in one reaction step in a so-called "one-pot process". A procedure is here followed in which either the triazolinone derivatives of the formula (X) are selected as starting compounds and these are reacted in succession with amines of the formula (VI) and subsequently with an acid in the "one-pot process" according to process (a) according to the invention, or, alternatively, the 1-unsubstituted triazoline hydrazones of the formula (VIII) are selected as starting compounds and these are reacted in succession with iso(thio)cyanates of the formula (IV) and subsequently with acid in the "one-pot process" according to process (a) according to the invention.

The reaction is carried out and the reaction products are worked up and isolated by known processes (compare in this context, for example, DE-OS (German Published Specification) 3,803,523, or the Preparation Examples).

Suitable diluents for carrying out process (b) according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dioxane, tetrahydrofuran or ethylene glycol dimethyl ether or ethylene glycol diethyl ether; ketones such as acetone, butanone or methyl isobutyl ketone; nitriles such as acetonitrile, propionitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate, or sulphoxides such as dimethyl sulphoxide.

If appropriate, process (b) according to the invention can be carried out in the presence of a suitable reaction auxiliary. Suitable reaction auxiliaries are all customary inorganic or organic bases. The following are preferably used: tertiary amines such as trimethylamine, triethylamine, tributylamine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU).

When carrying out process (b) according to the invention, the reaction temperatures can be varied within a substantial range. In general, the process is carried out at temperatures between 0° C. and +150° C., preferably at temperatures between +10° C. and +100° C.

For carrying out the process (b) according to the invention, 1.0 to 2.0 moles, preferably 1.0 to 1.5 moles, of iso(thio)cyanate of the formula (IV) and, if appropriate, 0.001 to 2.0 moles, preferably 0.001 to 1.0 mole, of reaction auxiliary are generally employed per mole of 1H-triazolinone of the formula (III).

The reaction is carried out and the reaction products are worked up and isolated by customary processes (compare, in this context, for example DE-OS (German Published Specification) 3,803,523, or the Preparation Examples. Suitable diluents for carrying out process (c) according to the invention are also inert organic solvents. The diluents mentioned in the case of process (b) are preferably used.

If appropriate, process (c) according to the invention can be carried out in the presence of a suitable basic reaction auxiliary. Suitable reaction auxiliaries are all customary inorganic or organic bases.

These include, for example, alkaline earth metal hydroxides or alkali metal hydroxides, such as sodium hydroxide, calcium hydroxide, potassium hydroxide and also ammonium hydroxide, alkali metal carbonates such as sodium carbonate, potassium carbonate, potassium hydrogen carbonate, sodium hydrogen carbonate or ammonium carbonate, alkali metal acetates or alkaline earth metal acetates such as sodium acetate, potassium acetate, calcium acetate or ammonium acetate, and also tertiary amines such as trimethylamine, triethylamine, tributylamine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU).

When carrying out process (c) according to the invention, the reaction temperatures can be varied within a substantial range. In general, the process is carried out at temperatures between 0° C. and +120° C., preferably at temperatures between +20° C. and +50° C.

Process (c) according to the invention is customarily carried out under atmospheric pressure.

For carrying out process (c) according to the invention, 1.0 to 5.0 moles, preferably 1.0 to 2.5 moles, of base are generally employed as reaction auxiliary per mole of triazolinone of the formula (V).

The reaction is carried out and the reaction products are worked up and isolated by known processes (compare, in this context, for example DE-OS (German Published Specification) 3,803,523, or the Preparation Examples.

The end products of the formula (I) are purified with the aid of customary processes, for example by column chromatography or by recrystallisation. They are characterised with the aid of the melting point or, in the case of compounds which do not crystallise, with the aid of proton nuclear resonance spectroscopy ($^1$H-NMR).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the qenera: Echinochloa, Setaria, Panicum, Digitaria, Phleum, Poa, Festuca, Eleusine, Brachiaria, Lolium, Bromus, Avena, Cyperus, Sorghum, Agropyron, Cy:odon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective combating of weeds in annual cultures.

In this context, the active compounds according to the invention can be employed with particularly good success for combating monocotyledon and dicotyledon weeds in monocotyledon and dicotyledon cultures such as, for example, wheat, maize, soya beans, cotton or oilseed rape.

In addition, the active compounds according to the invention also engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amount of active compound applied to the plants or their environment and the way in which the compounds are applied. In each case, growth regulators are intended to influence the crop plants in the particular manner desired.

The amount of leaf on plants can be controlled under the influence of growth regulators so that defoliation of the plants at a desired point in time is achieved. Such defoliation is of great importance in the mechanical harvesting of cotton, but also of interest for facilitating harvesting in other crops, such as, for example, in viticulture. Defoiiation of the plants can also be carried out to lower the transpiration of plants before they are transplanted.

The active compounds can be converted into the customary formulations, such as solutions, emulsions, suspensions, powders, foams, pastes, granules, aerosols, natural and synthetic materials impregnated with active compound, and very fine capsules in polymeric substances.

These formulations are produced in a known manner, for example by mixing the active compounds with extenders, that is liquid solvents, liquified gases under pressure and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide or dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fat&y alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3(2,2-dimethylpropyl)-1,3,5-triazine-2,4(1H,3H)-dione (AMETHYDIONE) or N-(2-benzothiazolyl)-N,N,-dimethylurea (METABENZTHIAZURON) for combating weeds in cereals; 4-amino-3-methyl-6-phenyl-1,2,4-triazin-5(4H)-one (METAMITRON) for combating weeds in sugar beet, and 4-amino-6(1,1-dimethylethyl)-3-methylthio-1,2,4-triazin-5(4H)-one (METRIBUZIN) for combating weeds in soya beans. Mixtures with 2,4-dichlorophenoxyacetic acid (2,4-D); 4 -(2,4-dichlorophenoxy)-butyric acid (2,4-DB); 2,4-dichlorophenoxypropionic acid (2,4-DP); (2-methyl-4-chlorophenoxy)-acetic acid (MCPA); (4-chloro-2-methylphenoxy)propionic acid (MCPP); [(4-amino-3,5-dichloro-6-fluoro-2-pyridinyl)-oxy]-acetic acid or its 1-methylheptyl ester (FLUROXYPYR); 2-[4-(2,4-dichlorophenoxy)phenoxy]-propionic acid, its methyl or its ethyl ester (DICLOFOP); 2-{4-[(6-chloro-2-benzoxazolyl)-oxy]-phenoxy}-propanoic acid, its methyl or ethyl ester (FENOXAPROP); 2-[4-(5-trifluoromethyl-2-pyridyloxy)-phenoxy]-propanoic acid or its butyl ester (FLUAZIFOP); ethyl 2-[4-(6-chloroquinoxalin-2-yl-oxy)-phenoxy]-propionate (QUIZALOFOPETHYL); 2-{4-[(3-chloro-5-(trifluoromethyl)-2-pyridinyl)-oxy]-phenoxy}-propanoic acid or its ethyl ester (HALOXYFOP); 3,6-dichloro-2-pyridincarboxylic acid (CLOPYRALID); 5-amino-4-chloro-2-phenyl-2,3-dihydro-3-oxy-pyridazine (CHLORIDAZON); 3-(ethoxycarbonylaminophenyl) N-(3,-methylphenyl)-carbamate (PHENMEDIPHAM); isopropyl N-phenyl-carbamate (PROPHAM); N-(3-chlorophenyl)-isopropyl-carbamate (CHLORPROPHAM); 4-amino-benzenesulphonyl-methyl-carbamate (ASULAM); 2,6-diethyl-N-(methoxymethyl)-chloroacetanilide (ALACHLOR); N-(butoxymethyl)-2-chloro-N-(2,6-diethylphenyl)-acetamide (BUTACHLOR); 2-chloro-N-(2,6-dimethylphenyl)-N-[(1H)-pyrazol-1-yl-methyl]-acetamide (METAZACHLOR); 2-ethyl-6-methyl-N-(1-methyl-2-methoxyethyl)-chloroacetanilide (METOLACHLOR); 4-(di-n-propylamino)-3,5-dinitrobenzenesulphonamide (ORYZALIN); N-(1-ethylpropyl)-3,4-dimethyl-2,6-dinitroaniline (PENDIMETHALIN); 2,6-dinitro-4-trifluoromethyl-N,N-dipropylaniline (TRIFLURALIN); 5-(2-chloro-4-trifluoromethyl-phenoxy)-2-nitro-benzoic acid (ACIFLUORFEN); methyl5-(2,4-dichlorophenoxy)-2-nitrobenzoate(BIFENOX); 5-(2-chloro-4-trifluoromethyl-phenoxy)-N-methylsulphonyl-2-nitrobenzamide (FOMESAFEN); 2-ethoxy-1-methyl-2-oxoethyl 5-[2-chloro-4-(trifluoromethyl)-phenoxy]-2-nitrobenzoate (LACTOFEN); 2-chloro-4-trifluoromethylphenyl 3-ethoxy-4-nitro-phenyl ether (OXYFLUORFEN); N,N-dimethyl-N'-(3-chloro-4-methylphenyl)-urea (CHLORTOLURON); N,N-dimethyl-N'-(3-trifluoromethylphenyl)-urea (FLUOMETURON); N,N-dimethyl-N'-(4-isopropylphenyl)-urea (ISOPROTURON); methyl-6,6-dimethyl-2,4-dioxo-3-[1-(2-propenyloxyamino)-butylidene]-cyclohexanecarboxylic acid (ALLOXYDIM); 2-[1-ethoximino)-butyl]-3-hydroxy-5-[tetrahydro-(2H)-thio-pyran-3-yl]-2-cyclohexen-1-one (CYCLOXYDIM); 2-[1-(ethoxamino)-butylidene]-5-(2-ethylthiopropyl)-1,3-cyclohexadione (SETHOXYDIM); 2-[4,5-dihydro-4-methyl-4-isopropyl-5-oxo-(1H)-imidazol-2-yl]5-ethyl-pyridine-3-carboxylic acid (IMAZETHAPYR); methyl 2-[4,5-dihydro-4-methyl-4-(1-methylethyl)-5-oxo-1H-imidazol-2-yl]-4(5)-methylbenzoate (IMAZAMETHABENZ); 2-[5-methyl-5-(1-methylethyl)-4-oxo-2-imidazolin-2-yl]-3-quinoxaline carboxylic acid (IMAZAQUIN); 3,5-dibromo-4-hydroxy-benzonitrile (BROMOXYNIL); 3,5-diiodo-4-hydroxybenzonitrile (IOXYNIL); N-methyl-2-(1,3-benzothiazol-2-yloxy)-acetanilide (MEFENACET); ethyl 2-{[(4-chloro-6-methoxy-2-pyrimidinyl)-aminocarbonyl]-aminosulphonyl}-benzoate (CHLORIMURON); 2-chloro-N-{[(4-methoxy-6-methyl-1,3,5-triazin-2-yl)-amino]-carbonyl}-benzenesulphonamide (CHLORSULFURON); 2-([[(4-methoxy-6 -methyl-1,3,5-triazin-2-yl)-amino)-carbonyl]-amino]-sulphonyl}-benzoic acid or its methyl ester (METSULFURON); methyl 3-[[[[(4-methoxy-6-methyl-1,3,5-triazin-2-yl)-amino]-carbonyl]-amino]-sulphonyl]-thiophene-2-carboxylate (THIAMETURON); N,S-diethyl-N-cyclohexyl-thiocarbamate (CYCLOATE); S-ethyl N,N-di-n-propyl-thiocarbamate (EPTAME); S-(2,3,3-trichloroallyl}N,N-diisopropylthiocarbamate (TRIALLATE); 2-chloro-4-ethylamino-6-isopropylamino-1,3,5-triazine (ATRAZIN); 2-chloro-4-ethylamino-6-(3-cyanopropylamino)-1,3,5-triazine (CYANAZIN); 2-chloro-4,6-bis-(ethylamino)-1,3,5-triazine (SIMAZIN); 2,4-bis-[N-ethylamino]-6-methylthio-1,3,5-triazine (SIMETRYNE); 4-ethylamino-2-t-butylamino-6-methylthio-s-triazine (TERBUTRYNE); 4-amino-6-t-butyl-3-ethylthio-1,2,4-triazine-5(4H)-one (ETHIOZIN); 3-cyclohexyl-6-dimethylamino-1-methyl-1,3,5-triazine-2,4-dione (HEXAZINONE); 3-isopropyl-2,1,3 TM benzothiadiazin-4-one 2,2-dioxide (BENTAZONE); exo-1-methyl-4-(1-methylethyl)-2-(2-methylphenyl-methoxy)-7-oxabicyclo(2,2,1)-heptane (CINMETHYLIN); 0-(6-chloro-3-phenylpyridazin-4-yl) S-octyl thiocarbonate (PYRIDATE) or 2-[(2-chlorophenyl)-methyl]-4,4-dimethylisoxazolidin-3-one (DIMETHAZONE) may also be advantageous. Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.001 and 10 kg of active compound per hectare of soil surface, preferably between 0.005 and 5 kg per hectare.

The preparation and use of the active compounds according to the invention can be seen from the following examples.

PREPARATION EXAMPLES

Example I-1

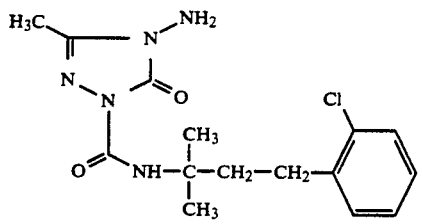

(Process a)

To 4.2 g (0.01 mol) of 4-(4-methylpent-2-yliden-imino)-3-methyl-1-[2-methyl-4-(2-chlorophenyl)-but-2-yl-aminocarbonyl]-1,2,4-triazolin-5-one in 100 ml of ethanol there are added 20 ml of water and 5 ml of concentrated hydrochloric acid, and the mixture is stirred for 3 hours at 60° C. and 200 mbar. For working-up, the solution is concentrated in vacuo, the residue is taken up in dichloromethane, and the solution is washed with saturated sodium hydrogen carbonate solution, dried over sodium sulphate and reconcentrated in vacuo. The residue is brought to crystallisation by trituration with petroleum ether, filtered off and dried.

1.7 g (50 % of theory) of 4-amino-3-methyl-1-[2-methyl-4-(2-chlorophenyl)-but-2-yl-aminocarbonyl]-1,2,4-triazolin-5-one of melting point 102° C. are obtained.

Preparation of the starting compound

Example II-1

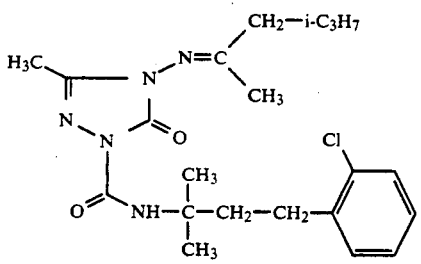

To 3.9 g (0.02 mol) of 4-(4-methylpent-2-yliden-imino)-3-methyl-1,2,4-triazolin-5-one in 100 ml of acetonitrile there are added 0.2 g of diazabicycloundecene (DBU) and 4.5 g (0.02 mol) of 2-methyl-4-(2-chlorophenyl)-but-2-yl isocyanate, and the mixture is stirred for 18 hours at 20° C. For working-up, the solvent is distilled off in vacuo, the oily residue is digested with petroleum ether, supernatant petroleum ether is decanted off, and the residue is freed from volatile components under a high vacuum.

8.1 g (97 % of theory) of 4-(4-methylpent-2-ylidenimino)-3-methyl-1-[2-methyl-4-(2-chlorophenyl)-but-2-yl-aminocarbonyl]-1,2,4-triazolin-5-one of melting point 79° C. are obtained.

Example VIII-1

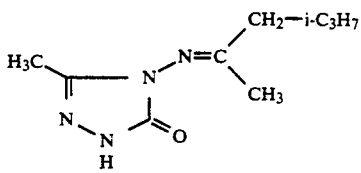

A mixture of 114 g (1.0 mol) of 4-amino-3-methyl-1,2,4-triazolin-5-one (compare, for example, DE-OS (German Published Specification) 3,803,523), 2 g of p-toluene-sulphonic acid and 500 ml of 4-methylpentan-2-one is refluxed for 4 hours in a water separator. For working-up, the mixture is concentrated in vacuo, the residue is brought to crystallisation by trituration with petroleum ether; the crystals are filtered off and dried.

187 g (95 % of theory) of 4-(4-methylpent-2-ylidenimino)-3-methyl-1,2,4-triazolin-5-one of melting point 91° C. are obtained.

Example I-2

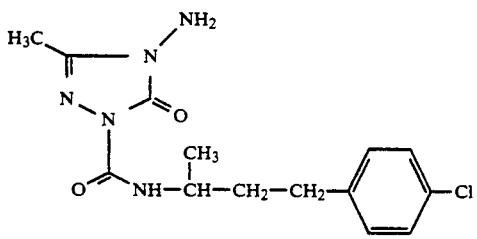

(Process a)

A mixture of 6.1 g (0.015 mol) of 4-(4-methylpent-2-yliden-imino)-3-methyl-1-[4-(4-chlorophenyl)-but-2-ylaminocarbonyl]-1,2,4-triazolin-5-one, 50 ml of ethanol, 25 ml of water and 5 ml of concentrated hydrochloric acid is stirred for 3 hours at 60° C. and 200 mbar. For working-up, the mixture is concentrated under a water pump vacuum, the residue is taken up in 200 ml of dichloromethane, the solution is washed with 200 ml of saturated aqueous sodium hydrogen carbonate solution, the organic phase is dried over magnesium sulphate and filtered, and the filtrate is freed from solvent in vacuo.

3.4 g (70 % of theory) of 4-amino-3-methyl-1-[4-(4-chlorophenyl)-but-2-yl-aminocarbonyl]-1,2,4-triazolin-5-one is obtained as an oil.

$^1$H-NMR (CDCl$_3$/tetramethylsilane): δ=1.26 (d,J=7 Hz); 2.33 (s) ppm.

Synthesis of the starting compound

Example II-2

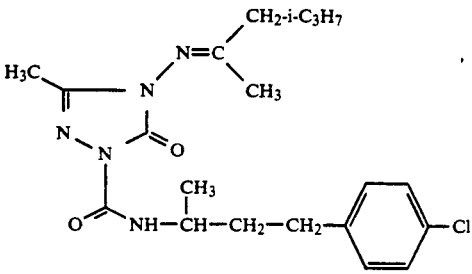

6.3 g (0.02 mol) of 4-(4-methylpent-2-yliden-imino)-3-methyl-1-phenoxycarbonyl-1,2,4-triazolin-5-one and 3.7 g (0.02 mol) of 4-(4-chlorophenyl)-but-2-ylamine in 100 ml of tetrahydrofuran are stirred for 18 hours at 20° C., the mixture is subsequently concentrated in vacuo, the residue is taken up in dichloromethane, washed several times with aqueous sodium hydrogen carbonate solution, dried over sodium sulphate and filtered, and the filtrate is freed from solvent in vacuo.

7.0 g (86 % of theory) of 4-(4-methylpent-2-ylidenimino)-3-methyl-1-[4-(4-chlorophenyl)-but-2-yl-aminocarbonyl]-1,2,4-triazolin-5-one is obtained as an oil.

$^1$H-NMR (CDCl$_3$/tetramethylsilane): δ=1.26 (d,J=7 Hz); 2.0 (s); 2.24 (s) ppm.

Example X-1

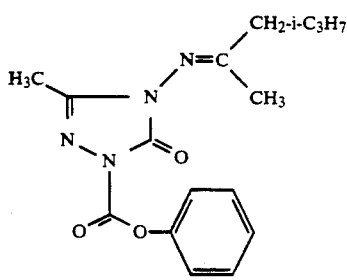

To a mixture of 98 g (0.5 mol) of 4-(4-methylpent-2-yliden-imino)-3-methyl-1,2,4-triazolin-5-one, 625 ml of dichloromethane, 22 g (0.55 mol) of sodium hydroxide, 625 ml of water and 4 g of tetrabutylammonium bromide there are added dropwise, with stirring, 86.1 g (0.55 mol) of phenyl chloroformate, the mixture is subsequently stirred for 18 hours at 20° C., the organic phase is then separated off, washed with water, dried over sodium sulphate and concentrated in vacuo. The residue is brought to crystallisation by trituration with diethyl ether, and the crystals which have formed are filtered off and dried.

83.7 g (53 % of theory) of 4-(4-methylpent-2-ylidenimino)-3-methyl-1-phenoxycarbonyl-1,2,4-triazolin-5-one of melting point 114° C. are obtained.

Example I-3

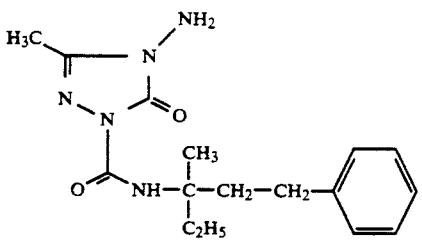

[Process (a) "one-pot variant"]

To 3.9 g (0.02 mol) of 4-(4-methylpent-2-yliden-imino)-3-methyl-1,2,4-triazolin-5-one in 100 ml of dichloromethane there are added, in succession, 0.1 g of diazabicycloundecene (DBU) and 4.1 g (0.02 mol) of 3-methyl-1-phenyl-pent-3-yl isocyanate, and the mixture is stirred for 18 hours at 20° C. The solvent is subsequently removed in vacuo, the residue is taken up in 100 ml of ethanol, the solution is treated with 20 ml of water and 5 ml of concentrated hydrochloric acid and stirred for 3 hours at 60° C. and 200 mbar. For working-up, the solvent is distilled off in vacuo, the residue is taken up in dichloromethane, and the solution is washed with saturated aqueous sodium hydrogen carbonate solution, dried over sodium sulphate and concentrated in vacuo. The residue is brought to crystallisation by trituration with petroleum ether, filtered off and dried.

5.2 g (82 % of theory) of 4-amino-3-methyl-1-(3-methyl-1-phenyl-pent-3-yl-aminocarbonyl)-1,2,4-triazolin-5-one of melting point 78° C. are obtained.

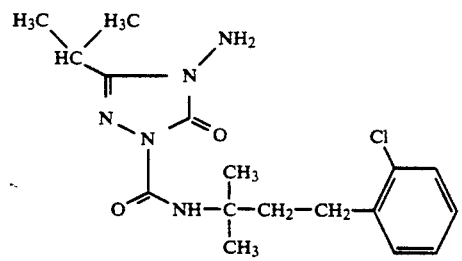

(Process b)

To 1.4 g (0.01 mol) of 4-amino-3-isopropyl-1,2,4-triazolin-5-one (compare, for example, DE-OS (German Published Specification) 3,803,523) in 100 ml of acetonitrile there are added 1 ml of diazabicycloundecene (DBU) and 2.2 g (0.01 mol) of 2-methyl-4-(2-chlorophenyl)-but-2-yl isocyanate, the mixture is subsequently stirred for 18 hours at 40° C. and then cooled to room temperature, and the product which has been obtained in crystalline form is filtered off.

1.4 g (38 % of theory) of 4-amino-3-isopropyl-1-[2-methyl-4-(2-chlorophenyl)-but-2-yl-aminocarbonyl]-1,2,4-triazolin-5-one of melting point 159° C. are obtained.

Synthesis of the starting compound

Example IV-1

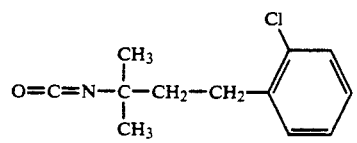

To 150 g (1.5 mol) of phosgene in 2.5 l of chlorobenzene there is added dropwise at 15° C. with stirring a solution of 198 g (1.0 mol) of 1,1-dimethyl-3-(2-chlorophenyl)-propylamine in 1.0 l of chlorobenzene, during which process the temperature of the reaction mixture rises to 25° C. When the addition is complete, the mixture is heated to 70° C. and the stirred mixture is slowly heated to reflux temperature while more phosgene is passed in (approx. 50 g/hour), and stirring is continued for 30 minutes at this temperature. For working-up, approx. 1 l of chlorobenzene is distilled off together with excess phosgene, and the residue is concentrated under a water pump vacuum and distilled under a high vacuum.

212 g (95 % of theory) of 2-methyl-4-(2-chlorophenyl)-but-2-yl isocyanate of boiling point 83° C. at 0.1 mbar are obtained.

Example VI-1

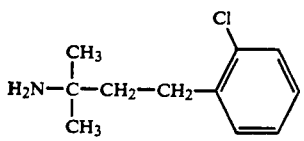

In a stirred autoclave, 40.6 g (0.21 mol) of 3-amino-3,3-dimethyl-1-(2-chlorophenyl)-1-propine together with 10 g of Raney-Nickel and 250 ml of tetrahydrofuran are treated with hydrogen up to a pressure of 50 bar, and the stirred mixture is then gradually heated to 40° C. while keeping constant a hydrogen pressure of 50 bar. For working-up, the mixture is filtered, the filtrate is concentrated under a water pump vacuum, and the residue is distilled under a high vacuum.

31.8 g (77% of theory) of 3-amino-3,3-dimethyl-1-(2-chlorophenyl)-1-propane of refractive index $n_D^{21} = 1.4817$ are obtained.

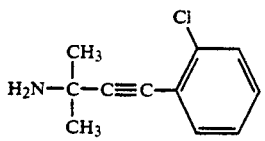

To 96.7 g (0.5 mol) of 1-bromo-2-chloro-benzene and 45.7 g (0.55 mol) of 3-amino-3,3-dimethyl-1-propine in 500 ml of triethylamine there are added 7.0 g (0.01 mol) of palladium(II) bis-triphenylphosphine-dichloride, 7.6 g (0.04 mol) of copper(I) iodide and 21.0 g (0.4 mol) of triphenylphosphine, the mixture is refluxed for 24 hours and subsequently filtered, and the filtrate is concentrated under a water pump vacuum. The residue is partitioned between dichloromethane (approx. 300 ml) and water (approx. 300 ml), and the organic phase is separated off, dried over sodium sulphate and filtered. The filtrate is concentrated under a water pump vacuum and distilled under a high vacuum.

74.1 g (75 % of theory) of 3-amino-3,3-dimethyl-1-(2-chlorophenyl)-1-propine of refractive index $n_D^{21} = 1.5799$ are obtained.

The following substituted triazolinones of the general formula (I)

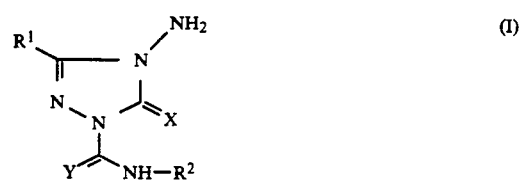

are obtained in a corresponding manner and following the general instructions for synthesis:

| Example No. | R¹ | R² | X | Y | Physical properties |
|---|---|---|---|---|---|
| I-5 | C₂H₅ | —C(CH₃)₂—CH₂—CH₂—C₆H₅ | O | O | ¹H NMR*): 1.46; 2.03–2.13; 2.6–2.7 |
| I-6 | cyclopropyl | —C(CH₃)₂—CH₂—CH₂—C₆H₅ | O | O | m.p. 129° C. |
| I-7 | i-C₃H₇ | —C(CH₃)₂—CH₂—CH₂—C₆H₅ | O | O | m.p. 87° C. |
| I-8 | i-C₃H₇ | —CH(CH₃)—CH₂—CH₂—C₆H₅ | O | O | $n_D^{20} = 1.5365$ |
| I-9 | i-C₃H₇ | —C(CH₃)₂—CH₂—CH₂—CH₂—C₆H₅ | O | O | m.p. 79° C. |
| I-10 | CH₃ | —C(CH₃)₂—CH₂—CH₂—CH₂—C₆H₅ | O | O | ¹H NMR*): 1.38; 2.3 |
| I-11 | CH₃ | —C(CH₃)₂—CH₂—CH₂—C₆H₄—OCH₃ | O | O | ¹H NMR*): 1.44; 3.27; 3.75 |

-continued

| Example No. | R¹ | R² | X | Y | Physical properties |
|---|---|---|---|---|---|
| I-12 | i-C$_3$H$_7$ | -CH(n-C$_4$H$_9$)-CH$_2$-CH$_2$-C$_6$H$_5$ | O | O | n$_D^{20}$ = 1.5209 |
| I-13 | CH$_3$ | -CH(n-C$_4$H$_9$)-CH$_2$-CH$_2$-C$_6$H$_5$ | O | O | m.p. 84° C. |
| I-14 | CH$_3$ | cyclopropyl-phenyl (methylcyclopropyl attached to phenyl) | O | O | m.p. 152° C. |
| I-15 | CH$_3$ | -CH(CH$_3$)-CH(C$_2$H$_5$)-CH$_2$-C$_6$H$_4$-4-Cl | O | O | m.p. 122-123° C. |
| I-16 | CH$_3$ | -CH(CH$_3$)-CH(CH$_3$)-CH$_2$-C$_6$H$_4$-4-Cl | O | O | m.p. 118-119° C. |
| I-17 | CH$_3$ | -CH(CH$_3$)-CH$_2$-CH$_2$-C$_6$H$_4$-4-CH$_3$ | O | O | ¹H NMR*): 1.25; 2.30; 2.31 |
| I-18 | CH$_3$ | -CH(CH$_3$)-CH$_2$-CH$_2$-C$_6$H$_4$-4-OCH$_3$ | O | O | ¹H NMR*): 2.33; 3.77 |
| I-19 | CH$_3$ | -CH(CH$_3$)-CH$_2$-CH$_2$-C$_6$H$_4$-2-Cl | O | O | ¹H NMR*): 1.28; 2.33 |
| I-20 | CH$_3$ | -CH(CH$_3$)-CH$_2$-CH$_2$-C$_6$H$_3$-3,4-Cl$_2$ | O | O | ¹H NMR*): 1.26; 2.34 |
| I-21 | CH$_3$ | -CH(CH$_3$)-CH$_2$-CH$_2$-C$_6$H$_3$-2,4-Cl$_2$ | O | O | m.p. 98° C. |
| I-22 | CH$_3$ | -CH(CH$_3$)-CH$_2$-CH$_2$-C$_6$H$_4$-3-Cl | O | O | ¹H NMR*): 1.27; 2.32 |
| I-23 | CH$_3$ | -CH(CH$_3$)-CH$_2$-CH$_2$-C$_6$H$_4$-3-CH$_3$ | O | O | ¹H NMR*): 1.26; 2.31; 2.32 |

-continued
| Example No. | R¹ | R² | X | Y | Physical properties |
|---|---|---|---|---|---|
| I-24 | CH₃ | 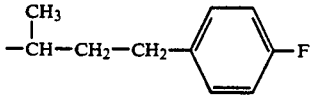 | O | O | ¹H NMR*): 1.26; 2.33 |
| I-25 | CH₃ | 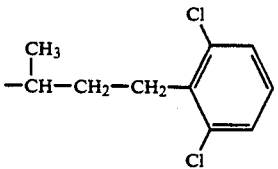 | O | O | m.p. 75° C. |
| I-26 | CH₃ | 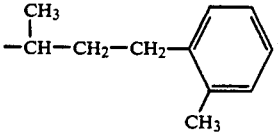 | O | O | m.p. 94° C. |
| I-27 | i-C₃H₇ | 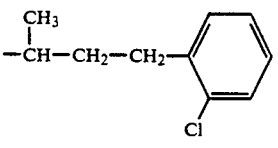 | O | O | ¹H NMR*): 1.28; 1.35 |
| I-28 | i-C₃H₇ | 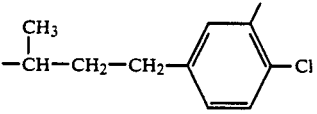 | O | O | ¹H NMR*): 1.26; 1.35 |
| I-29 | i-C₃H₇ | 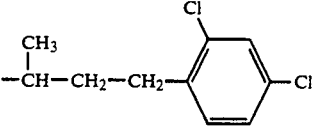 | O | O | ¹H NMR*): 1.27; 1.34 |
| I-30 | i-C₃H₇ | 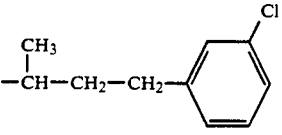 | O | O | ¹H NMR*): 1.27; 1.35 |
| I-31 | i-C₃H₇ | 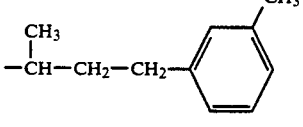 | O | O | ¹H NMR*): 1.27; 1.34; 2.31 |
| I-32 | i-C₃H₇ | 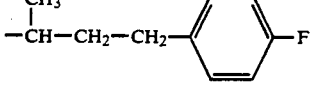 | O | O | ¹H NMR*): 1.26; 1.35 |
| I-33 | i-C₃H₇ | 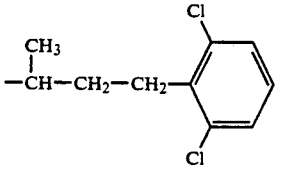 | O | O | ¹H NMR*): 1.34; 1.7–1.95; 2.9–3.22 |

-continued

| Example No. | R¹ | R² | X | Y | Physical properties |
|---|---|---|---|---|---|
| I-34 | i-C₃H₇ | -CH(CH₃)-CH₂-CH₂-(2-CH₃-C₆H₄) | O | O | ¹H NMR*): 1.29; 1.34; 2.30 |
| I-35 | cyclopropyl | -CH(CH₃)-CH₂-CH₂-(4-Cl-C₆H₄) | O | O | m.p. 110° C. |
| I-36 | cyclopropyl | -CH(CH₃)-CH₂-CH₂-(2-Cl-C₆H₄) | O | O | m.p. 125° C. |
| I-37 | cyclopropyl | -CH(CH₃)-CH₂-CH₂-(3,4-Cl₂-C₆H₃) | O | O | ¹H NMR*): 1.24 |
| I-38 | cyclopropyl | -CH(CH₃)-CH₂-CH₂-(2,4-Cl₂-C₆H₃) | O | O | m.p. 81° C. |
| I-39 | cyclopropyl | -CH(CH₃)-CH₂-CH₂-(3-Cl-C₆H₄) | O | O | ¹H NMR*): 1.24 |
| I-40 | cyclopropyl | -CH(CH₃)-CH₂-CH₂-(3-CH₃-C₆H₄) | O | O | ¹H NMR*): 1.24 |
| I-41 | cyclopropyl | -CH(CH₃)-CH₂-CH₂-(2,6-Cl₂-C₆H₃) | O | O | m.p. 118° C. |
| I-42 | cyclopropyl | -CH(CH₃)-CH₂-CH₂-(2,3-(CH₃)₂-C₆H₃) | O | O | m.p. 117° C. |
| I-43 | cyclopropyl | -CH(CH₃)-CH₂-CH₂-(4-OCH₃-C₆H₄) | O | O | ¹H NMR*): 3.71 |
| I-44 | i-C₃H₇ | -CH(CH₃)-CH₂-CH₂-(4-Cl-C₆H₄) | O | O | ¹H NMR*): 1.27; 1.35 |

-continued

| Example No. | R¹ | R² | X | Y | Physical properties |
|---|---|---|---|---|---|
| I-45 | cyclopropyl | −C(CH₃)(C₂H₅)−CH₂−CH₂−(3-CH₃-C₆H₄) | O | O | ¹H NMR*): 1.40; 2.30 |
| I-46 | i-C₃H₇ | −CH(CH₃)−CH₂−CH₂−(4-OCH₃-C₆H₄) | O | O | ¹H NMR*): 3.66 |
| I-47 | i-C₃H₇ | −C(CH₃)(C₂H₅)−CH₂−CH₂−(3-CH₃-C₆H₄) | O | O | ¹H NMR*): 1.40; 2.31 |
| I-48 | CH₃ | −C(CH₃)(CH₃)−CH₂−CH₂−(3-CH₃-C₆H₄) | O | O | ¹H NMR*): 1.45; 2.29; 2.30 |
| I-49 | i-C₃H₇ | −C(CH₃)(CH₃)−CH₂−CH₂−(3-CH₃-C₆H₄) | O | O | ¹H NMR*): 1.45; 2.31 |
| I-50 | cyclopropyl | −C(CH₃)(CH₃)−CH₂−CH₂−(3-CH₃-C₆H₄) | O | O | m.p. 107° C. |
| I-51 | C₂H₅ | −C(CH₃)(CH₃)−CH₂−CH₂−(3-CH₃-C₆H₄) | O | O | ¹H NMR*): 1.45; 2.31 |
| I-52 | C₂H₅ | −C(CH₃)(C₂H₅)−CH₂−CH₂−(3-CH₃-C₆H₄) | O | O | ¹H NMR*): 1.41; 2.31 |
| I-53 | i-C₃H₇ | −CH(CH₃)−CH₂−CH₂−(4-CH₃-C₆H₄) | O | O | ¹H NMR*): 1.26; 1.35 |
| I-54 | cyclopropyl | −CH(CH₃)−CH₂−CH₂−(4-CH₃-C₆H₄) | O | O | ¹H NMR*): 1.24; 2.29 |
| I-55 | cyclopropyl | −CH(CH₃)−CH₂−CH₂−(4-F-C₆H₄) | O | O | m.p. 107° C. |

-continued

| Example No. | R¹ | R² | X | Y | Physical properties |
|---|---|---|---|---|---|
| I-56 | $CH_3$ | −C($C_2H_5$)($C_2H_5$)−$CH_2$−$CH_2$−C₆H₅ | O | O | m.p. 89° C. |
| I-57 | $CH_3$ | −$CH_2$−$CH_2$−$CH_2$−C₆H₅ | O | O | m.p. 65° C. |
| I-58 | $CH_3$ | −CH($CH_3$)−$CH_2$−$CH_2$−C₆H₄($CF_3$) (o-) | O | O | ¹H NMR*): 2.25 |
| I-59 | i-$C_3H_7$ | −CH($CH_3$)−$CH_2$−$CH_2$−C₆H₄($CF_3$) (o-) | O | O | ¹H NMR*): 1.36; 1.8–1.95 2.7–2.8 |
| I-60 | i-$C_3H_7$ | −C($CH_3$)($CH_3$)−$CH_2$−$CH_2$−C₆H₄($CH_3$) (o-) | O | O | m.p. 86° C. |
| I-61 | i-$C_3H_7$ | −C($CH_3$)($CH_3$)−$CH_2$−$CH_2$−C₆H₄−Cl (p-) | O | O | m.p. 130° C. |
| I-62 | i-$C_3H_7$ | −$CH_2$−$CH_2$−$CH_2$−C₆H₅ | O | O | m.p. 79° C. |
| I-63 | $CH_3$ | −C($CH_3$)($C_2H_5$)−$CH_2$−$CH_2$−C₆H₄($CH_3$) (m-) | O | O | ¹H NMR*): 1.39; 2.28; 2.30 |
| I-64 | $CH_3$ | −C($CH_3$)($CH_3$)−$CH_2$−$CH_2$−C₆H₄($CH_3$) (o-) | O | O | m.p. 122° C. |
| I-65 | $CH_3$ | −C($CH_3$)($C_2H_5$)−$CH_2$−$CH_2$−C₆H₄($CH_3$) (o-) | O | O | m.p. 118° C. |
| I-66 | $CH_3$ | −C($CH_3$)($CH_3$)−$CH_2$−$CH_2$−C₆H₄−Cl (p-) | O | O | m.p. 125° C. |

-continued

| Example No. | R¹ | R² | X | Y | Physical properties |
|---|---|---|---|---|---|
| I-67 | $CH_3$ | -C(CH₃)₂-CH₂-CH₂-(2,6-dichlorophenyl) | O | O | m.p. 156° C. |
| I-68 | $CH_3$ | -C(CH₃)₂-CH₂-CH₂-(4-fluorophenyl) | O | O | m.p. 161° C. |
| I-69 | $CH_3$ | -C(CH₃)₂-CH₂-CH₂-(4-methylphenyl) | O | O | m.p. 109° C. |
| I-70 | $CH_3$ | -CH(CH₃)-C(CH₃)₂-CH₂-(4-methylphenyl) | O | O | m.p. 80° C. |
| I-71 | $CH_3$ | -C(CH₃)₂-C(CH₃)₂-CH₂-(4-methylphenyl) | O | O | m.p. 137° C. |
| I-72 | $CH_3$ | -C(CH₃)₂-CH₂-CH₂-(3-chlorophenyl) | O | O | m.p. 110° C. |
| I-73 | $CH_3$ | -C(CH₃)₂-CH₂-CH₂-(2,4-dichlorophenyl) | O | O | m.p. 143° C. |
| I-74 | $CH_3$ | -C(CH₃)₂-CH₂-CH₂-(3,4-dichlorophenyl) | O | O | m.p. 119° C. |
| I-75 | $i$-$C_3H_7$ | -C(C₂H₅)₂-CH₂-CH₂-phenyl | O | O | m.p. 94° C. |
| I-76 | $i$-$C_3H_7$ | -C(C₂H₅)(CH₃)-CH₂-CH₂-phenyl | O | O | m.p. 87° C. |
| I-77 | $i$-$C_3H_7$ | -C(CH₃)₂-CH₂-CH₂-(4-methylphenyl) | O | O | m.p. 127° C. |
| I-78 | $i$-$C_3H_7$ | -CH(CH₃)-C(CH₃)₂-CH₂-(4-methylphenyl) | O | O | m.p. 121° C. |

-continued

| Example No. | R¹ | R² | X | Y | Physical properties |
|---|---|---|---|---|---|
| I-79 | i-C₃H₇ | −C(CH₃)₂−C(CH₃)₂−CH₂−(4-CH₃-C₆H₄) | O | O | m.p. 86° C. |
| I-80 | i-C₃H₇ | −C(CH₃)₂−CH₂−CH₂−(3-Cl-C₆H₄) | O | O | m.p. 78° C. |
| I-81 | i-C₃H₇ | −C(CH₃)₂−CH₂−CH₂−(2,6-Cl₂-C₆H₃) | O | O | m.p. 124° C. |
| I-82 | i-C₃H₇ | −C(CH₃)₂−CH₂−CH₂−(2,4-Cl₂-C₆H₃) | O | O | m.p. 123° C. |
| I-83 | i-C₃H₇ | −C(CH₃)₂−CH₂−CH₂−(3,4-Cl₂-C₆H₃) | O | O | m.p. 78° C. |
| I-84 | i-C₃H₇ | −C(CH₃)₂−CH₂−CH₂−(4-F-C₆H₄) | O | O | m.p. 95° C. |
| I-85 | cyclopropyl | −C(C₂H₅)₂−CH₂−CH₂−C₆H₅ | O | O | ¹H NMR*): 2.4–2.6 |
| I-86 | cyclopropyl | −C(CH₃)(C₂H₅)−CH₂−CH₂−C₆H₅ | O | O | ¹H NMR*): 1.39 |
| I-87 | cyclopropyl | −C(CH₃)₂−CH₂−CH₂−(4-CH₃-C₆H₄) | O | O | m.p. 144° C. |
| I-88 | CH₃ | −C(CH₃)₂−CH₂−CH₂−(3-pyridyl) | O | O | ¹H NMR*): 1.48; 2.31 |
| I-89 | i-C₃H₇ | −C(CH₃)₂−CH₂−CH₂−(3-pyridyl) | O | O | ¹H NMR*): 1.34; 1.45 |
| I-90 | cyclopropyl | −CH(CH₃)−C(CH₃)₂−CH₂−(4-CH₃-C₆H₄) | O | O | m.p. 76° C. |

-continued

| Example No. | R¹ | R² | X | Y | Physical properties |
|---|---|---|---|---|---|
| I-91 | cyclopropyl | -C(CH₃)(CH₃)-C(CH₃)(CH₃)-CH₂-C₆H₄-4-CH₃ | O | O | m.p. 76° C. |
| I-92 | cyclopropyl | -C(CH₃)(CH₃)-CH₂-C₆H₄-3-Cl | O | O | m.p. 95° C. |
| I-93 | cyclopropyl | -C(CH₃)(CH₃)-CH₂-CH₂-C₆H₄-4-F | O | O | m.p. 135° C. |
| I-94 | C₂H₅ | -C(C₂H₅)(C₂H₅)-CH₂-CH₂-C₆H₅ | O | O | ¹H NMR*): 1.31; 2.80 |
| I-95 | C₂H₅ | -C(CH₃)(C₂H₅)-CH₂-CH₂-C₆H₅ | O | O | ¹H NMR*): 140 |
| I-96 | C₂H₅ | -C(CH₃)(CH₃)-CH₂-CH₂-C₆H₄-4-CH₃ | O | O | m.p. 103° C. |
| I-97 | C₂H₅ | -C(CH₃)(CH₃)-CH₂-CH₂-C₆H₄-3-Cl | O | O | m.p. 88° C. |
| I-98 | C₂H₅ | -C(CH₃)(CH₃)-CH₂-CH₂-C₆H₄-4-F | O | O | m.p. 116° C. |
| I-99 | C₂H₅ | -CH(CH₃)-C(CH₃)(CH₃)-CH₂-C₆H₄-4-CH₃ | O | O | m.p. 114° C. |
| I-100 | C₂H₅ | -C(CH₃)(CH₃)-C(CH₃)(CH₃)-CH₂-C₆H₄-4-CH₃ | O | O | ¹H NMR*): 2.32 |
| I-101 | C₂H₅ | -C(CH₃)(CH₃)-CH₂-CH₂-C₆H₄-3-CN | O | O | m.p. 152° C. |
| I-102 | CH₃ | -CH(CH₃)-C(CH₃)(CH₃)-CH₂-C₆H₃-3,4-Cl₂ | O | O | ¹H NMR*): 3.05–3.2; 3.9–4.05 |

-continued

| Example No. | R¹ | R² | X | Y | Physical properties |
|---|---|---|---|---|---|
| I-103 | CH₃ | -C(CH₃)₂-CH₂-CH₂-C₆H₄-CN | O | O | m.p. 149–150° C. |
| I-104 | CH₃ | -C(CH₃)₂-CH₂-CH₂-C₆H₃(CF₃)(Cl) | O | O | m.p. 152° C. |
| I-105 | CH₃ | -C(C₂H₅)(CH₃)-CH₂-CH₂-C₆H₄-Cl | O | O | m.p. 80° C. |
| I-106 | CH₃ | -C(CH₃)₂-CH₂-CH₂-C₆H₄-COOC₂H₅ | O | O | ¹H NMR*): 1.46; 2.29 |
| I-107 | CH₃ | -CH(CH₃)-CH₂-C(CH₃)₂-C₆H₄-Cl | O | O | ¹H NMR*): 1.27; 1.43; 2.3 |
| I-108 | CH₃ | -C(CH₃)₂-CH₂-CH₂-C₆H₄-COOC₂H₅ | O | O | ¹H NMR*): 1.45; 2.28 |
| I-109 | CH₃ | -CH₂-CH₂-C(CH₃)₂-C₆H₄-Cl | O | O | m.p. 58° C. (decomp.) |
| I-110 | i-C₃H₇ | -CH(CH₃)-C(CH₃)₂-CH₂-C₆H₃Cl₂ | O | O | m.p. 60° C. (decomp.) |
| I-111 | CH₃ | -C(CH₃)₂-CH₂-CH₂-C₆H₃(OCF₂CF₂O) | O | O | m.p. 71–74° C. |
| I-112 | CH₃ | -C(CH₃)₂-CH₂-CH₂-C₆H₄-COO-n-C₃H₇ | O | O | ¹H NMR*): 2.27; 4.20–4.30 |
| I-113 | CH₃ | -C(CH₃)₂-CH₂-CH₂-C₆H₃(Cl)(CH₃) | O | O | m.p. 131° C. |

-continued
| Example No. | R¹ | R² | X | Y | Physical properties |
|---|---|---|---|---|---|
| I-114 | CH₃ | 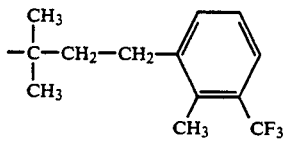 | O | O | m.p. 143° C. |
|  |  | 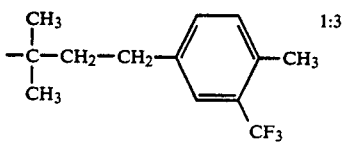 1:3 |  |  |  |
| I-115 | CH₃ | 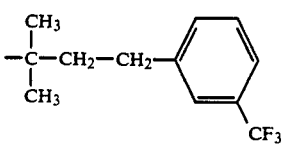 | O | O | m.p. 127° C. |
| I-116 | CH₃ | 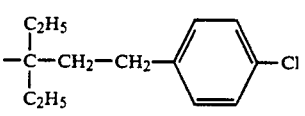 | O | O | m.p. 112° C. |
| I-117 | CH₃ | 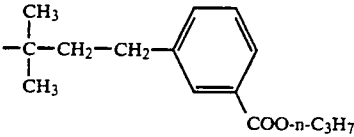 | O | O | ¹H NMR*): 1.47; 2.31 |
| I-118 | CH₃ | 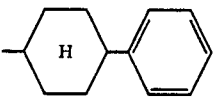 | O | O | m.p. 156° C. |
| I-119 | i-C₃H₇ | 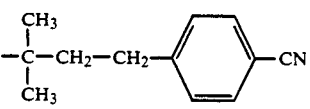 | O | O | m.p. 138-140° C. |
| I-120 | CH₃ | 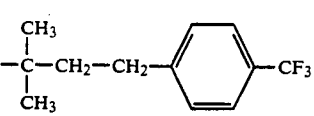 | O | O | m.p. 122° C. |
| I-121 | CH₃ | 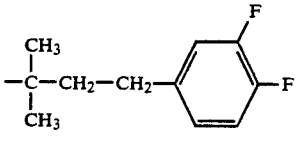 | O | O | m.p. 118° C. |
| I-122 | i-C₃H₇ | 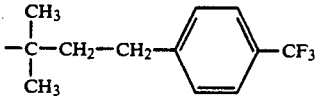 | O | O | m.p. 146° C. |
| I-123 | i-C₃H₇ | 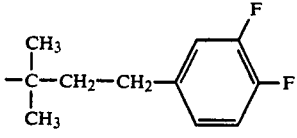 | O | O | m.p. 93° C. |

-continued

| Example No. | R¹ | R² | X | Y | Physical properties |
|---|---|---|---|---|---|
| I-124 | CH₃ | cyclohexyl-C(CH₃)-C≡C-(4-Cl-C₆H₄) | O | O | m.p. 164° C. |
| I-125 | i-C₃H₇ | cyclohexyl-C(CH₃)-C≡C-(4-Cl-C₆H₄) | O | O | m.p. 145° C. |
| I-126 | i-C₃H₇ | -C(CH₃)₂-CH₂-CH₂-(3-COO-n-C₃H₇-C₆H₄) | O | O | ¹H NMR*): 0.95–1.05; 1.46 |
| I-127 | i-C₃H₇ | 4-phenylcyclohexyl (H) | O | O | m.p. 105° C. |
| I-128 | i-C₃H₇ | -CH₂-CH₂-C(CH₃)₂-(4-Cl-C₆H₄) | O | O | m.p. 117° C. |
| I-129 | i-C₃H₇ | -C(CH₃)₂-CH₂-CH₂-(4-C(CH₃)₃-C₆H₄) | O | O | m.p. 110° C. |
| I-130 | CH₃ | -C(CH₃)₂-CH₂-CH₂-(4-C(CH₃)₃-C₆H₄) | O | O | m.p. 120° C. |
| I-131 | i-C₃H₇ | -C(CH₃)₂-CH₂-CH₂-(3,4-(OCF₂CF₂O)-C₆H₃) | O | O | m.p. 118° C. |
| I-132 | i-C₃H₇ | -C(CH₃)₂-CH₂-CH₂-(3-CF₃-C₆H₄) | O | O | m.p. 81° C. |
| I-133 | i-C₃H₇ | -C(CH₃)₂-CH₂-CH₂-(4-COO-n-C₃H₇-C₆H₄) | O | O | ¹H NMR*): 1.46; 1.70–1.90 |

-continued

| Example No. | R¹ | R² | X | Y | Physical properties |
|---|---|---|---|---|---|
| I-134 | i-C₃H₇ | -C(CH₃)₂-CH₂-CH₂-(2-CH₃,4-Cl-phenyl); -C(CH₃)₂-CH₂-CH₂-(2-CH₃,3-CF₃-phenyl) | O | O | m.p. 129° C. |
| I-135 | i-C₃H₇ | -C(CH₃)₂-CH₂-CH₂-(2-CF₃,3-CF₃-phenyl) 1:3 | O | O | m.p. 119° C. |
| I-136 | i-C₃H₇ | -C(C₂H₅)₂-CH₂-CH₂-(4-Cl-phenyl) | O | O | m.p. 142° C. |
| I-137 | i-C₃H₇ | -C(CH₃)₂-CH₂-CH₂-(3-CN-phenyl) | O | O | m.p. 98–99° C. |
| I-138 | i-C₃H₇ | -C(CH₃)₂-CH₂-CH₂-(2-CF₃,4-Cl-phenyl) | O | O | m.p. 103° C. |
| I-139 | i-C₃H₇ | -C(CH₃)(C₂H₅)-CH₂-CH₂-(4-Cl-phenyl) | O | O | m.p. 127° C. |
| I-140 | i-C₃H₇ | -C(CH₃)₂-CH₂-CH₂-(3-COOC₂H₅-phenyl) | O | O | ¹H NMR*): 1.46; 4.3–4.42 |
| I-141 | i-C₃H₇ | -CH(CH₃)-CH₂-C(CH₃)₂-(4-Cl-phenyl) | O | O | ¹H NMR*): 3.04–3.2; 4.25 |
| I-142 | i-C₃H₇ | -C(CH₃)₂-CH₂-CH₂-(4-COOC₂H₅-phenyl) | O | O | ¹H NMR*): 1.44; 3.02–3.17 |
| I-143 | i-C₃H₇ | -CH(CH₃)-CH(CH₃)-CH₂-(4-Cl-phenyl) | O | O | m.p. 117° C. |

-continued

| Example No. | R¹ | R² | X | Y | Physical properties |
|---|---|---|---|---|---|
| I-144 | $C_2H_5$ | $-CH(CH_3)-CH_2-CH_2-C_6H_4-Cl$ | O | O | ¹H NMR*): 1.82–1.9; 2.65–2.75; 7.1–7.15; 7.6–7.65 |
| 145 | $CH_3$ | $-C(CH_3)_2-CH_2-CH_2-C_6H_4-CHF_2$ | O | O | ¹H-NMR*): 1,45; 4,32; 6,39, 6,58; 6,77. |
| 146 | $CH_3$ | $-C(CH_3)_2-CH_2-CH_2-C_6H_4-C_2H_5$ | O | O | Fp. 106° C. |
| 147 | $i\text{-}C_3H_7$ | $-C(CH_3)_2-CH_2-CH_2-C_6H_4-C_2H_5$ | O | O | Fp. 133° C. |
| 148 | $i\text{-}C_3H_7$ | $-C(CH_3)_2-CH_2-CH_2-C_6H_4-CHF_2$ | O | O | Fp. 131° C. |
| 149 | $CH_3$ | $-C_6H_{10}-C(CH_3)_2-C_6H_5$ | O | O | ¹H-NMR*): 1,27; 2,28; 4,55. |
| 150 | $i\text{-}C_3H_7$ | $-C_6H_{10}-C(CH_3)_2-C_6H_5$ | O | O | ¹H-NMR*): 3,0–3,2; 4,47; 7,1–7,35. |
| 151 | $i\text{-}C_3H_7$ | $-CH(CH_3)-CH(CH_3)-CH_2-C_6H_5$ | O | O | ¹H-NMR*): 0,85–0,93; 1,33–1,38; 4,35; 7,15–7,30; |
| 152 | $CH_3$ | $-CH_2-CH(CH_3)-CH_2-C_6H_4-C(CH_3)_3$ | O | O | Fp. 123–125° C. |

*) The ¹H NMR spectra were recorded in deuterochloroform (CDCl₃) or hexadeuterodimethyl sufoxide (DMSO-d₆) with tetramethylsilane (TMS) as the internal standard. The δ value represents the chemical shift in ppm.

Use Examples

In the following Use Examples, the compound given below was employed as comparison substance:

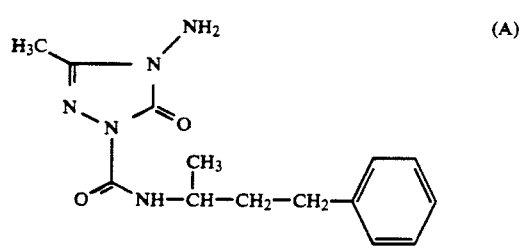

(A)

1-(phenyl-2-butylaminocarbonyl)-3-methyl-4-amino-1,2,4-triazolin-5-one (compare, for example, DE-OS (German Published Specification) 3,719,575).

Example A

Pre-emergence test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desire concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, a clearly superior activity and crop plant selectivity compared with the prior art is shown, for example, by the compounds of the following Preparation Examples: I-9, I-32, I-35 and I-59.

Example B

Post-emergence test

| Solvent: | 5 parts by weight of acetone |
| --- | --- |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control. The figures denote:

0%=no action (like untreated control)
100%=total destruction

In this test, a clearly superior activity and crop plant selectivity compared with the prior art is shown, for example, by the compounds of the formula I of the following Preparation Examples: I-2, I-5, I-7, I-8, I-9, I-10, I-18, I-22, I-30, I-31, I-32, I-35, I-37, I-39, I-43, I-44, I-48, I-53, I-54, I-55, I-58, I-59, I-66, I-69, I-72, I-73, I-74, I-76, I-80, I-83 and I-84.

It will be understood that the specification and examples are illustrative but not limitative of the present invention and that other embodiments within the spirit and scope of the invention will suggest themselves to those skilled in the art.

What is claimed is:

1. A substituted triazolinone of the formula (I)

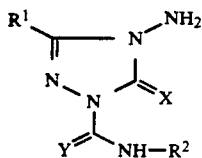

in which
$R^1$ represents alkyl or cycloalkyl,
$R^2$ represents cycloalkyl which is optionally substituted by aryl, arylalkyl, arylalkenyl or arylalkinyl wherein the aryl moiety has from 6 to 10 carbon atoms, or represents a radical of the formula

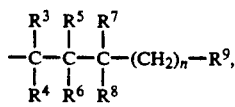

X represents oxygen or sulphur and
Y represents oxygen or sulphur, where
$R^3$, $R^4$, $R^5$, $R^6$, $R^7$ and $R^8$ represent hydrogen or alkyl,
$R^9$ represents in each case optionally substituted cycloalkyl, phenyl or naphthyl and
n represents a number 0, 1, 2 or 3,
but with the exception of those compounds in which, simultaneously, $R^1$ represents a methyl radical, X represents oxygen, Y represents oxygen and $R^2$ represents a radical of the formula

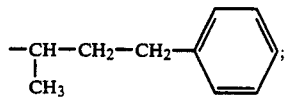

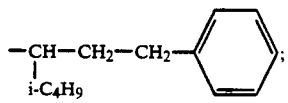

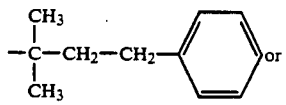

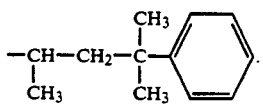

2. A substituted triazolinone, according to claim 1 in which
$R^1$ represents a straight-chain or branched alkyl having 1 to 6 carbon atoms or cycloalkyl having 3 to 7 carbon atoms,
$R^2$ represents cycloalkyl which has 3 to 7 carbon atoms and which is optionally monosubstituted or polysubstituted by identical or different substituents selected from the group consisting of aryl, arylalkyl, arylalkenyl and arylalkinyl, each of which has 6 to 10 carbon atoms in the aryl moiety and up to 6 carbon atoms in the respective straight-chain or branched alkyl or alkenyl or alkinyl moieties and each of which is optionally monosubstituted or polysubstituted by identical or different substituents selected from the group consisting of halogen, cyano, nitro, in each case straight-chain or branched alkyl, alkoxy and alkylthio, each of which has 1 to 4 carbon atoms, in each case straight-chain or branched halogenalkyl, halogenalkoxy or halogenalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted or polysubstituted by identical or different substituents from the series comprising halogen and/or straight-chain or branched alkyl having 1 to 4 carbon atoms, $R^2$ furthermore represents a radical of the formula

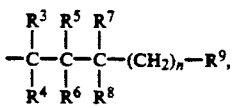

X represents oxygen or sulphur and
Y represents oxygen or sulphur, where
$R^3$ represents straight-chain or branched alkyl having 1 to 8 carbon atoms,
$R^4$, $R^5$, $R^7$ and $R^8$ independently of each other in each case represents hydrogen or straight-chain or branched alkyl having 1 to 4 carbon atoms,
$R^9$ represents cycloalkyl which has 3 to 7 carbon atoms and which is optionally monosubstituted or polysubstituted by identical or different substituents selected from the group consisting of halogen, cyano, in each case straight-chain or branched alkyl having 1 to 4 carbon atoms and in each case straight-chain or branched halogenalkyl having in each case 1 to 4 carbon atoms and 1 to 9 identical or different halogen atoms;
$R^9$ furthermore represents phenyl or naphthyl optionally monosubstituted or polysubstituted by identical or different substituents selected from the group consisting of
halogen, cyano, nitro, in each case straight-chain or branched alkyl, alkoxy or alkylthio, each of which has 1 to 4 carbon atoms, in each case straight-chain or branched halogenalkyl, halogenalkoxy or halogenoalkylthio, each of which has 1 to 4 carbon atoms and 1 to 9 identical or different halogen atoms; divalent, straight-chain or branched dioxyalkylene which has 1 to 3 carbon atoms and which is optionally monosubstituted to tetrasubstituted by identical or different halogen substituents; dialkylamino, N-alkanoylamino, alkoxycarbonyl or alkoximinoalkyl, each of which has 1 to 4 carbon atoms in individual straight-chain or branched alkyl moieties, and aryl or aryloxy which has 6 to 10 carbon atoms and which is in each case optionally monosubstituted or polysubstituted by identical or different substituents form the series comprising halogen and/or straight-chain or branched alkyl having 1 to 4 carbon atoms, and n represents a number 0, 1, 2 or 3.

3. Substituted triazolinones according to claim 1, in which
$R^1$ represents methyl, ethyl, n- or i-propyl, n-, i-, s- or t-butyl, cyclopropyl, cyclobutyl, cyclopentyl or cyclohexyl,
$R^2$ represents cyclopropyl, cyclobutyl, cyclopentyl or cyclohexyl, each of which is optionally monosubstituted or disubstituted by identical or different substituents selected from the group consisting of phenyl, benzyl, phenylethyl, phenylpropyl, phenylethenyl, phenylpropenyl, phenylethinyl, phenylpropinyl, α-naphthyl or β-naphthyl, each of which is optionally monosubstituted to trisubstituted in the aryl moiety by identical or different substituents selected from the group consisting of
fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, meth-ylthio, ethylthio, trifluoromethyl, trifluoromethoxy, trifluoromethylthio, methoxycarbonyl, ethoxycarbonyl, methoximinomethyl, methoximinoethyl, ethoxyiminomethyl, ethoximinoethyl, and phenyl which is optionally monosubstituted to trisubstituted by identical or different substituents selected from the group consisting of fluorine, chlorine, bromine, methyl and ethyl, $R^2$ furthermore represents a radical of the formula

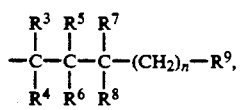

X represents oxygen or sulphur and
Y represents oxygen or sulphur, where
$R^3$ represents straight-chain or branched alkyl having 1 to 6 carbon atoms,
$R^4$, $R^5$, $R^6$, $R^7$ and $R^8$ represent hydrogen or straight-chain or branched alkyl having 1 to 3 carbon atoms,
$R^9$ represents cyclopropyl, cyclobutyl, cyclopentyl or cyclohexyl, each of which is optionally monosubstituted to pentasubstituted by identical or different substituents selected from the group consisting of
fluorine, chlorine, bromine, cyano, methyl, ethyl, n- or i-propyl, chloromethyl, dichloromethyl, trichloromethyl, difluoromethyl and trifluoromethyl;
$R^9$ further represents phenyl, α-naphthyl, β-naphthyl, each of which is optionally monosubstituted to trisubstituted by identical or different substituents selected from the group consisting of fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, difluoromethyl, trifluoromethyl, difluoromethoxy, trifluoromethoxy, difluoromethylthio, trifluoromethylthio, dimethylamino, diethylamino, N-acetamido, dioxymethylene, difluorodioxymethylene, dioxyethylene, trifluorodioxyethylene, tetrafluorodioxyethylene, methoxycarbonyl, ethoxycarbonyl, propoxycarbonyl, methoximinomethyl, methoximinoethyl, ethoximinomethyl, ethoximinoethyl, or phenyl, phenoxy, α-naphthyl or β-naphthyl each of which is optionally monosubstituted to trisubstituted by identical or different substituents selected from the group consisting of fluorine, chlorine, bromine, methyl, ethyl, methoxy and ethoxy, and n represents a number 0, 1 or 2.

4. A substituted triazolinone according to claim 1, in which
$R^1$ represents methyl, ethyl, n- or i-propyl or cyclopropyl,
$R^2$ represents a radical of the formula

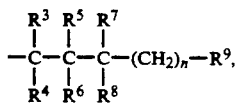

X represents oxygen,
Y represents oxygen,
$R^3$ represents methyl, ethyl, n- or i-propyl, n-, i-, s- or t-butyl, R⁴, R⁵, R⁶, R⁷ and R⁸ independently of each other in each case represents hydrogen, methyl or ethyl, R⁹ represents phenyl which is optionally monosubstituted to trisubstituted by identical or different substituents selected from the group consisting of fluorine, chlorine, bromine, cyano, nitro, methyl, ethyl, n- and i-propyl, n-, i-, s- and t-butyl, methoxy, ethoxy, n- and i-propoxy, n-, i-, s- and t-butoxy, methylthio, ethylthio, difluoromethyl, trifluoromethyl, difluoromethoxy, trifluoro-methoxy, difluoromethylthio, trifluoromethylthio, dimethylamino, diethylamino, N-acetamido, dioxymethylene, difluorodioxymethylene, dioxyethylene, trifluorodioxyethylene, tetrafluorodioxyethylene, methoxycarbonyl, ethoxycarbonyl, propoxycarbonyl, methoximinomethyl, methoximinoethyl, ethoximinomethyl, ethoximinoethyl, phenyl, phenoxy, α-naphthyl and β-naphthyl each of which is optionally monosubstituted or trisubstituted by identical or different substituents selected from the group consisting of fluorine, chlorine, bromine, methyl, ethyl, methoxy and ethoxy, and n represents a number 0 or 1.

5. A compound according to claim 1, wherein such compound is 4-amino-3-methyl-1[2-methyl-4-(ethylphenyl)-but-2-ylaminocarbonyl]-1,2,4-triazolin-5-on of the formula

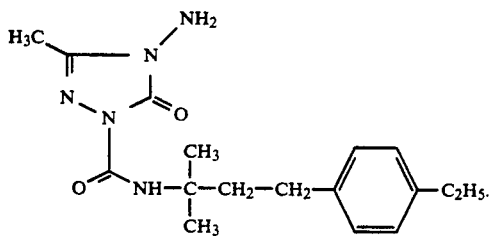

6. A compound according to claim 1, wherein such compound is 4-amino-3-isopropyl-1-[2-methyl-4-(4-difluoromethylphenyl)-but-2-yl-aminocarbonyl]-1,2,4-triazolin-5-on of the formula

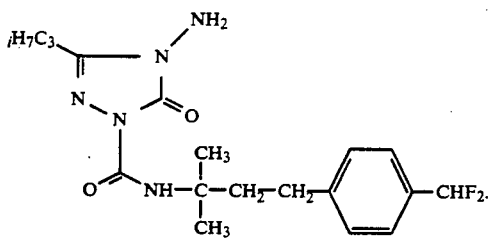

7. A compound according to claim 1, wherein such compound is 4-amino-3-methyl-1[4-phenyl]-cyclohexylaminocarbonyl-1,2,4-traizolin-5-on of the formula

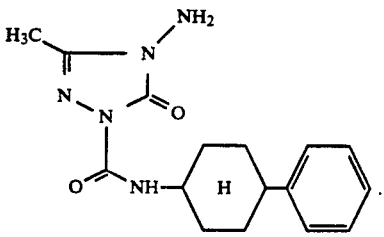

8. A compound according to claim 1, wherein such compound is 4-amino-3-cyclopropyl-1[4-chlorophenyl)-but-2-yl-aminocarbonyl]-1,2,4-traizolin-5-on of the formula

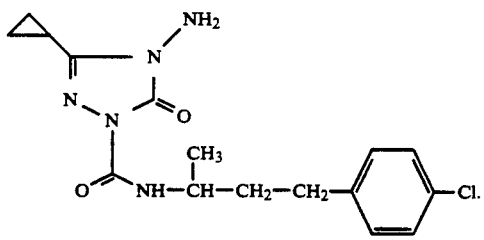

9. A compound according to claim 1, wherein such compound is 4-amino-3-isopropyl-1-[4-(3-trifluoromethylphenyl)-but-2-yl-aminocarbonyl]-1,2,4-triazolin-5-on of the formula

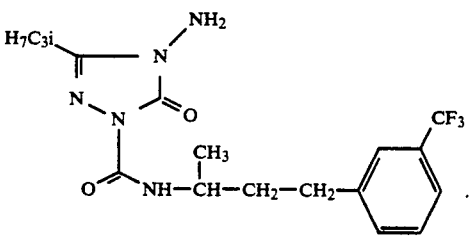

10. A compound according to claim 1, wherein such compound is 4-amino-3-isopropyl-1-[2-methyl-5phenyl-pent-2-yl-aminocarbonyl]-1,2,4-triazolin-5-on of the formula

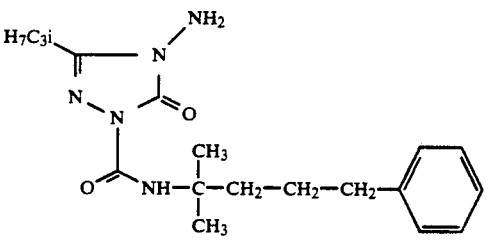

11. A compound comprising a herbicidally effective amount of a compound according to claim 1 and a diluent.

12. A method of combating unwanted vegetation which comprises applying to such vegetation or to a locus from which it is desired to exclude such vegetation a herbicidally effective amount of a compound according to claim 1.

13. The method according to claim 12 wherein such compound is
4-amino-3-methyl-1[2-methyl-4-(4-ethylphenyl)-but-2-yl-amino-carbonyl-1,2,4-triazoles-5-on, 4-amino-3-isopropyl-1[2-methyl-4-(4-difluoromethylphenyl)-but-2-yl-amino-carbonyl]-1,2,4-triazolin-5-on, 4-amino-3-methyl-1[4-phenyl]-cyclohexylaminocarbonyl-1,2,4-triazolin-5-on, 4-amino-3-cyclopropyl-1[4-(4-chlorophenyl)-but-2-ylaminocarbonyl]-1,2,4-triazolin-5-on, 4-amino-3-isopropyl-1[4-(3-trifluoromethylphenyl)-but-2-yl-aminocarbonyl]-1,2,4-triazolin-5-on, 4-amino-3-isopropyl-1[2-methyl-5-phenylpent-2-ylaminocarbonyl]-1,2,4-triazolin-5-on.

* * * * *

UNITED STATES PATENT AND TRADEMARK OFFICE
CERTIFICATE OF CORRECTION

PATENT NO. : 5,273,958
DATED : December 28, 1993
INVENTOR(S) : Kuhnt, et al.

It is certified that error appears in the above-indentified patent and that said Letters Patent is hereby corrected as shown below:

| | |
|---|---|
| Col. 52, lines 61-62 | Delete " halogenalkyl, halogenalkoxy or halogenalkylthio " and substitute -- halogenoalkyl, halogenoalkoxy or halogenoalkylthio -- |
| Col. 53, line 15 | After " $R^5$, " insert -- $R^6$, -- |
| Col. 53, line 24 | Delete " halogenalkyl " and substitute -- halogenoalkyl -- |
| Col. 53, line 34 | Delete " halogenalkyl, halogenalkoxy " and substitute -- halogenoalkyl, halogenoalkoxy -- |
| Col. 54, line 38 | Delete " or " (second occurrence) and substitute -- and -- |
| Col. 55, claim 5 lines 25-26 | Before " ethylphenyl " insert -- 4 --, after " 2-yl " insert -- - -- |
| Col. 56, line 2 | After " [4- " insert -- (4- -- |
| Col. 56, line 32 | After " 5 " insert -- - -- |

UNITED STATES PATENT AND TRADEMARK OFFICE
CERTIFICATE OF CORRECTION

PATENT NO. : 5,273,958
DATED : December 28, 1993
INVENTOR(S) : Kuhnt et al.

It is certified that error appears in the above-indentified patent and that said Letters Patent is hereby corrected as shown below:

Col. 56, line 57  After " carbonyl " insert -- ] --

Col. 56, line 63  After " yl " insert -- - --

Signed and Sealed this

Eleventh Day of July, 1995

Attest:

BRUCE LEHMAN

*Attesting Officer*    *Commissioner of Patents and Trademarks*